(12) United States Patent
Katoh et al.

(10) Patent No.: US 8,206,356 B2
(45) Date of Patent: Jun. 26, 2012

(54) REAGENT INJECTION APPARATUS AND METHOD OF PRODUCING THE SAME

(75) Inventors: Osamu Katoh, Toyohashi (JP); Estuo Tsuchikane, Toyohashi (JP); Atsushi Kureha, Nagoya (JP); Nobuyoshi Watanabe, Nagoya (JP)

(73) Assignees: ASAHI Intecc Co., Ltd., Nagoya (JP); Osamu Katoh, Nagoya (JP); Etsuo Tsuchikane, Toyohashi (JP)

( * ) Notice: Subject to any disclaimer, the term of this patent is extended or adjusted under 35 U.S.C. 154(b) by 1639 days.

(21) Appl. No.: 11/533,266

(22) Filed: Sep. 19, 2006

(65) Prior Publication Data
US 2007/0129706 A1    Jun. 7, 2007

(30) Foreign Application Priority Data
Sep. 21, 2005  (JP) ................. 2005-274423

(51) Int. Cl.
 *A61M 5/178*  (2006.01)
(52) U.S. Cl. .................. 604/164.13
(58) Field of Classification Search ....... 604/96.01–104, 604/164.01–164.13, 523, 264; 600/585
See application file for complete search history.

(56) References Cited

U.S. PATENT DOCUMENTS

| RE31,873 E | 4/1985 | Howes |
|---|---|---|
| 4,578,061 A | 3/1986 | Lemelson |
| 4,769,005 A | 9/1988 | Ginsburg et al. |
| 4,808,156 A | 2/1989 | Dean |
| 5,059,177 A | 10/1991 | Towne et al. |
| 5,190,528 A | 3/1993 | Fonger et al. |
| 5,261,889 A | 11/1993 | Laine et al. |
| 5,263,932 A | 11/1993 | Jang |
| 5,354,279 A | 10/1994 | Höfling |
| 5,413,581 A | 5/1995 | Goy |

(Continued)

FOREIGN PATENT DOCUMENTS

EP    1 070 513 A1    1/2001

(Continued)

OTHER PUBLICATIONS

Satoshi Taketani, "New Development of Cardiac Muscle Regeneration Therapy and Cardiac Failure Therapy," slides used at the Far Side Session held on Jun. 30, 2004 as a part of the 13th Annual Meeting of the Japanese Society of Interventional Cardiology, Jul. 1-3, 2004, with partially translated copies.

(Continued)

*Primary Examiner* — Matthew F DeSanto
(74) *Attorney, Agent, or Firm* — Knobbe Martens Olson & Bear LLP

(57) ABSTRACT

A structure includes a main tube 2 that contains a needlelike tubular body lumen 10 through which a needlelike tubular body 3 is inserted, with a distal section 4 of the main tube 2 having a first guide wire insertion section 33 and second guide wire insertion section 35, respectively containing a first guide wire lumen 38 and second guide wire lumen 52 through which a first guide wire 32 and second guide wire 34 are inserted. This structure further has a support tube 62 whose tip remains a free end, wherein this support tube 62 accepts a part of the second guide wire 34 extending out of the second guide wire lumen 52 and thereby supports the second guide wire insertion section 35.

13 Claims, 19 Drawing Sheets

U.S. PATENT DOCUMENTS

| | | | |
|---|---|---|---|
| 5,419,777 | A | 5/1995 | Höfling |
| 5,464,395 | A | 11/1995 | Faxon et al. |
| 5,702,384 | A | 12/1997 | Umeyama et al. |
| 5,797,869 | A | 8/1998 | Martin et al. |
| 5,906,594 | A | 5/1999 | Scarfone et al. |
| 5,916,194 | A | 6/1999 | Jacobsen et al. |
| 5,921,971 | A | 7/1999 | Agro et al. |
| 6,045,557 | A | 4/2000 | White et al. |
| 6,068,610 | A | 5/2000 | Ellis et al. |
| 6,068,638 | A | 5/2000 | Makower |
| 6,099,497 | A | 8/2000 | Adams et al. |
| 6,135,976 | A | 10/2000 | Tachibana et al. |
| 6,165,195 | A | 12/2000 | Wilson et al. |
| 6,217,554 | B1 | 4/2001 | Green |
| 6,248,122 | B1 | 6/2001 | Klumb et al. |
| 6,283,947 | B1 | 9/2001 | Mirzaee |
| 6,302,870 | B1 | 10/2001 | Jacobsen et al. |
| 6,375,615 | B1 | 4/2002 | Flaherty et al. |
| 6,440,161 | B1 | 8/2002 | Madrid et al. |
| 6,458,098 | B1 | 10/2002 | Kanesaka |
| 6,461,296 | B1 | 10/2002 | Desai |
| 6,544,230 | B1 | 4/2003 | Flaherty et al. |
| 6,547,767 | B1 | 4/2003 | Moein |
| 6,682,536 | B2 | 1/2004 | Vardi et al. |
| 6,682,556 | B1 | 1/2004 | Ischinger |
| 6,689,099 | B2 | 2/2004 | Mizaee |
| 6,692,466 | B1 | 2/2004 | Chow et al. |
| 6,706,017 | B1 | 3/2004 | Dulguerov |
| 6,884,258 | B2 | 4/2005 | Vardi et al. |
| 6,926,692 | B2 | 8/2005 | Katoh et al. |
| 7,387,639 | B2 * | 6/2008 | Bourang et al. ............ 623/1.11 |
| 7,985,204 | B2 * | 7/2011 | Katoh et al. ............ 604/164.01 |
| 2001/0011180 | A1 | 8/2001 | Fitzmaurice et al. |
| 2002/0055733 | A1 | 5/2002 | Wilson |
| 2002/0072706 | A1 | 6/2002 | Hiblar et al. |
| 2003/0040712 | A1 | 2/2003 | Ray et al. |
| 2003/0171714 | A1 * | 9/2003 | Katoh et al. ............... 604/96.01 |
| 2004/0064128 | A1 | 4/2004 | Raijman et al. |
| 2004/0073108 | A1 | 4/2004 | Saeed et al. |
| 2004/0102719 | A1 | 5/2004 | Keith et al. |
| 2004/0106866 | A1 | 6/2004 | Ookubo et al. |
| 2004/0176726 | A1 | 9/2004 | Katoh et al. |
| 2004/0176740 | A1 | 9/2004 | Chouinard |
| 2004/0220473 | A1 | 11/2004 | Lualdi |
| 2005/0004522 | A1 | 1/2005 | Katoh et al. |
| 2005/0070874 | A1 | 3/2005 | Masuda et al. |
| 2006/0025720 | A1 | 2/2006 | Sawa et al. |
| 2006/0184156 | A1 | 8/2006 | Jang |

FOREIGN PATENT DOCUMENTS

| | | |
|---|---|---|
| JP | 06-014997 | 1/1994 |
| JP | 08-317988 A | 12/1996 |
| JP | 2001-104487 | 4/2001 |
| JP | 2001-299927 | 10/2001 |
| JP | 2001-314514 | 11/2001 |
| JP | 2002-306606 | 10/2002 |
| JP | 2003-250899 A | 9/2003 |
| JP | 2003-339874 | 12/2003 |
| JP | 2004-267333 | 9/2004 |
| JP | 2004-267333 A | 9/2004 |
| WO | WO 92/10142 | 6/1992 |
| WO | WO 2004/098681 A1 | 5/2004 |
| WO | WO 2004-093963 | 11/2004 |
| WO | WO 2004/098681 A1 | 11/2004 |
| WO | WO 2004-107965 | 12/2004 |
| WO | WO 2006/043133 A2 | 4/2006 |

OTHER PUBLICATIONS

A poster used in a booth of Asahi Intecc Co., Ltd. at the 13th Annual Meeting of the Japanese Society of Interventional Cardiology, Jul. 1-3, 2004.

Etsuo Tsuchikane, "Percutaneous Cell Injection Device to the Myocardium," slides used at CCT2005 in Kobe, Sep. 27, 2005.

Japanese Office Action; Apr. 23, 2011; Application No. 2005-274423.

* cited by examiner

REAGENT INJECTION APPARATUS AND METHOD OF PRODUCING THE SAME

BACKGROUND OF THE INVENTION

1. Field of the Invention

The present invention relates to a reagent injection apparatus for injecting specified reagents into lesions and other locations in body tissues, as well as a production method of reagent injection apparatus thereof.

2. Description of the Related Art

Traditionally, various treatments, inspections, procedures and other medical manipulations have been conducted by inserting medial apparatuses, such as catheters, into blood vessels, gastrointestinal tract, urinal tract, and various other tubular organs and tissues in the patient's body. In recent years, treatments and other procedures are also carried out wherein reagent injection apparatuses such as reagent injection catheters are used to inject specified reagents into lesions in body tissues (Japanese Patent Laid-open No. 2001-299927 for an example).

These reagent injection apparatuses used in treatments and other procedures performed by means of reagent injection into lesions have a structure whereby a needlelike tubular body is inserted into a main tube in a manner movable in the axial direction. Also, such needlelike tubular body has an interior hole through which specified reagent can flow. With reagent injection apparatuses having this structure, the tip (needle) of the needlelike tubular body projects from the main tube that has been inserted into the blood vessels, in order to puncture the target lesion in body tissue and thereby inject specified reagent into the lesion through the interior hole in the needlelike tubular body.

For example, reagent injection apparatuses having the above structure include those equipped with two guide wires to smoothly puncture the target lesion in body tissue using the needle (Japanese Patent Laid-open No. 2004-267333 for an example).

Specifically, reagent injection apparatuses of such structure have one guide wire extending outward from the tip of the main tube, and another guide wire extending outward from the side face of the main tube. When the main tube has been inserted into one of two specified branching blood vessels, the guide wire extending out of the tip of the main tube is inserted into the branching blood vessel. On the other hand, the guide wire extending out of the side face of the main tube is inserted into the other branching blood vessel. In this condition, the needle is projected out of the main tube to puncture the target lesion in body tissue.

Such a reagent injection apparatus having two guide wires allow the two guide wires respectively inserted into the two branching blood vessels to receive the reactive force acting upon the needle, which generates when the needle punctures the body tissue. As a result, the needle can more reliably and smoothly puncture the body tissue to a desired depth compared to when a reagent injection apparatus equipped with only one guide wire is used.

In the use of these conventional reagent injection apparatuses, however, it is difficult, simply by inserting the two guide wires into the two branching blood vessels, to sufficiently suppress movement or rotation of the main tube around the axis caused by the reactive force generated when the needle punctures the body tissue or by any other acting force resulting from twisting or other movement of the needle. For the reason, in some cases sufficient effect cannot be obtained to operate the needle to smoothly puncture a specified position in body tissue to a desired depth, particularly in situations where the main tube must be stably positioned in the blood vessel to perform puncture operation, such as when puncturing the cardiac muscle or other relatively hard lesions with the needle. As a result, the aforementioned traditional apparatuses are used with a balloon provided on the main tube, and this balloon is inflated to ensure stable positioning inside the blood vessel.

SUMMARY OF THE INVENTION

In the above, if reagent injection apparatuses, equipped with a balloon on the main tube, have inside the main tube a total of four lumens, including three lumens for inserting a needlelike tubular body and two guide wires, respectively, and another lumen for supplying liquid to inflate the balloon, in a manner allowing the lumens to extend continuously over roughly the entire length of the main tube, these reagent injection apparatuses cannot sufficiently satisfy the requirement for diameter or size reduction that has been demanded by the operators to permit easier insertion of the apparatus into the patient's body.

Here, in view of the background described above, it is an object in an embodiment of the present invention to provide a reagent injection apparatus that permits more reliable and smoother puncturing of a specified position in body tissue to a specified depth using the tip of the needlelike tubular body, and also achieves diameter or size reduction in an advantageous manner. It is another object in an embodiment of the present invention to provide a method of producing such reagent injection apparatus in an advantageous manner.

To achieve one or more of the aforementioned objects, an embodiment of the present invention mainly provides a reagent injection apparatus characterized by comprising: (a) a main tube having flexibility, providing a needlelike tubular body lumen in a manner extending in an axial direction, and inserted into the patient's body; (b) a needlelike tubular body made of a flexible thin tube having an interior hole through which specified reagent can flow; wherein the needlelike tubular body is inserted into the needlelike tubular body lumen of the main tube in a manner movable in the axial direction; and wherein its tip section is projected outward from a projection hole provided in a distal section of the main tube to puncture specified tissue in the patient's body, in order to inject the reagent into the body tissue through the interior hole; (c) a first guide wire insertion section extending in the axial direction in the distal section of the main tube, and having a first guide wire lumen whose opening on distal side and opening on proximal side open in a manner sandwiching the projection hole; (d) a first guide wire inserted into the first guide wire lumen in the first guide wire insertion section in a manner movable in the axial direction; (e) a second guide wire insertion section extending in the axial direction in the distal section of the main tube, and having a second guide wire lumen whose opening on distal side and opening on proximal side open with a specified distance provided in between in the axial direction on a proximal side of the projection hole; (f) a second guide wire inserted into the second guide wire lumen in the second guide wire insertion section in a manner movable in the axial direction; and (g) a support tube having flexibility and having a tip section provided as a free end, wherein the support tube is provided in a manner branching from the main tube, and having in its interior a continuous lumen that continues to the second guide wire lumen through the opening on distal side in the second guide wire lumen, and wherein a part of the second guide wire extending from the opening on distal side in the second guide wire lumen is inserted into the continuous lumen in a manner movable in the axial direction.

To be specific, a reagent injection apparatus conforming to an embodiment allows, when the main tube is inserted into a blood vessel or other tubular organ branching into two parts, the tip of the needlelike tubular body to puncture a specified body tissue to inject reagent, by inserting the first guide wire into one of the two branching tubular organs and the second guide wire into the support tube to have the support tube support the wire, and then puncturing the body tissue with the needlelike tubular body while the second guide wire and support tube are both inserted into the other tubular organ. This way, the reactive force generated when the tip of needlelike tubular body punctures the body tissue or any other acting force resulting from twisting or other movement of the needlelike tubular body (hereinafter referred to as "reactive force of puncturing") can be received in an advantageous manner by not only the first guide wire and second guide wire, but also by the support tube.

Furthermore, such apparatus conforming to an embodiment has the first guide wire lumen, second guide wire lumen and continuous lumen positioned in the distal section of the main tube in a manner sandwiching a projection hole in between. Because of this, the tip of the needlelike tubular body projects through the projection hole virtually from inside a plane formed by the first guide wire and second guide wire. This way, the reactive force of puncturing is received more reliably by the plane formed by the first guide wire and second guide wire.

For the aforementioned reasons, such apparatus conforming to an embodiment suppresses in a more reliable manner any movement or rotation of the main tube around the axis due to the reactive force of puncturing that generates when the body tissue is punctured with the needlelike tubular body. As a result, even a large reactive force can be reliably received when puncturing the cardiac muscle and other relatively hard lesions with the needlelike tubular body, and thus in situations where the main tube must be stably positioned in the blood vessel, a specified position in body tissue can be punctured to a desired depth in a smooth manner.

In addition, a apparatus conforming to an embodiment virtually eliminates the need for a balloon as installed on the main tubes of conventional apparatuses, because the apparatus under an embodiment can reliably and sufficiently receive the reactive force of puncturing using the two guide wires and support tube, and is therefore able to exhibit higher supporting force of the main tube against the reactive force of puncturing. This means that the balloon lumen normally provided in the main tube to supply liquid to inflate the balloon can also be eliminated.

Moreover, in a reagent injection apparatus conforming to an embodiment all of its openings on distal side and proximal side in the first guide wire lumen and second guide wire lumen open in the distal section of the main tube. Therefore, except for this distal side a greater part of the remaining section of the main tube has a simple structure in which only a needlelike tubular body lumen is provided in its interior. This virtually reduces the number of lumens in the main tube.

For the aforementioned reasons, a reagent injection apparatus conforming to an embodiment not only permits smoother insertion into the patient's body through the use of a main tube of smaller diameter or size, but it also allows reagent to be injected more accurately into a lesion or other part of body tissue because the apparatus can be positioned stably in a desired position inside the patient's body to perform puncturing operation. Furthermore, a reagent injection apparatus conforming to an embodiment also provides an advantage of ensuring more stable blood flows, when the apparatus is used in a blood vessel, owing to the smaller diameter or size of the main tube.

In all of the aforesaid embodiments, any element used in an embodiment can interchangeably or additionally be used in another embodiment unless such a replacement or addition is not feasible or causes adverse effect. Further, the present invention can equally be applied to apparatuses and methods.

For purposes of summarizing the invention and the advantages achieved over the related art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

DESCRIPTION OF MAIN SYMBOLS IS AS FOLLOWS

Figure 1:
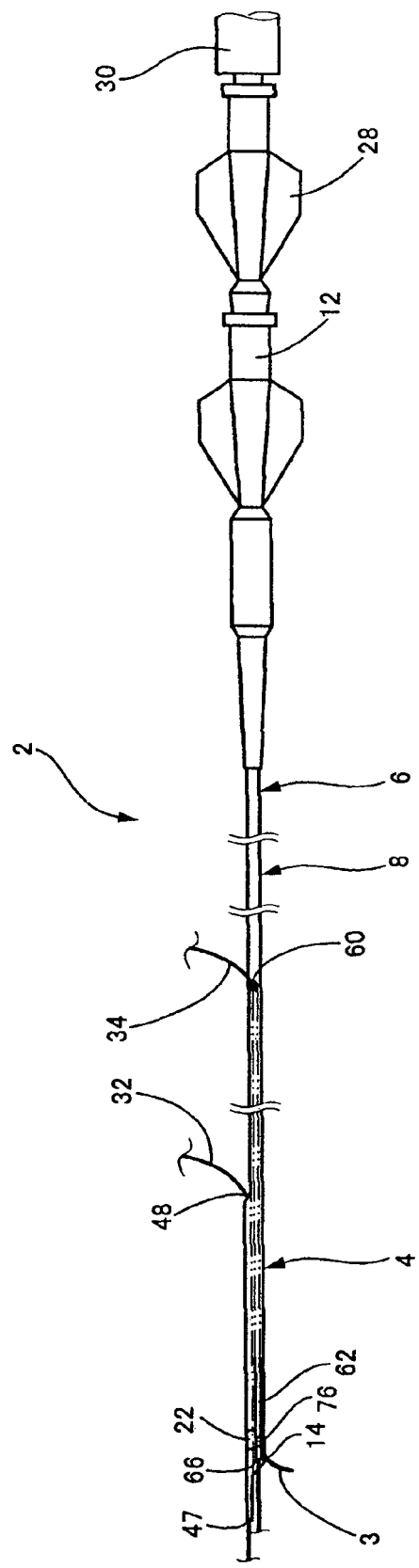
FIG. 1 is an explanatory drawing showing a front view of an example of a reagent injection apparatus based on a structure conforming to the present invention.

| | |
|---|---|
| 2 | Main tube |
| 3 | Needlelike tubular body |
| 4 | Distal section |
| 6 | Proximal section |
| 10 | Needlelike tubular body lumen |
| 14 | Projection hole |
| 32 | First guide wire |
| 33 | First guide wire insertion section |
| 34 | Second guide wire |
| 35 | Second guide wire insertion section |
| 36 | First guide wire insertion tube |
| 38 | First guide wire lumen |
| 47, 58 | Openings on distal side |
| 48, 60 | Openings on proximal side |
| 50 | Second guide wire insertion tube |
| 52 | Second guide wire lumen |
| 62 | Support tube |
| 64 | Continuous lumen |

DETAILED DESCRIPTION OF THE PREFERRED EMBODIMENT

The present invention will be explained with reference to preferred embodiments and drawings. However, the preferred embodiments and drawings are not intended to limit the present invention.

The present invention can be preferably implemented in the following embodiments:

1) A reagent injection apparatus characterized by comprising: (a) a main tube having flexibility, providing a needlelike tubular body lumen in a manner extending in an axial direction, and inserted into the patient's body; (b) a needlelike tubular body made of a flexible thin tube having an interior hole through which specified reagent can flow; wherein the needlelike tubular body is inserted into the needlelike tubular body lumen of the main tube in a manner movable in the axial direction; and wherein its tip section is projected outward from a projection hole provided in a distal section of the main tube to puncture specified tissue in the patient's body, in order to inject the reagent into the body tissue through the interior hole; (c) a first guide wire insertion section extending in the axial direction in the distal section of the main tube, and having a first guide wire lumen whose opening on distal side and opening on proximal side open in a manner sandwiching the projection hole; (d) a first guide wire inserted into the first guide wire lumen in the first guide wire insertion section in a manner movable in the axial direction; (e) a second guide wire insertion section extending in the axial direction in the distal section of the main tube, and having a second guide wire lumen whose opening on distal side and opening on proximal side open with a specified distance provided in between in the axial direction on a proximal side of the projection hole; (f) a second guide wire inserted into the second guide wire lumen in the second guide wire insertion section in a manner movable in the axial direction; and (g) a support tube having flexibility and having a tip section provided as a free end, wherein the support tube is provided in a manner branching from the main tube, and having in its interior a continuous lumen that continues to the second guide wire lumen through the opening on distal side in the second guide wire lumen, and wherein a part of the second guide wire extending from the opening on distal side in the second guide wire lumen is inserted into the continuous lumen in a manner movable in the axial direction.

2) A reagent injection apparatus characterized by comprising: (a) a main tube having flexibility, providing a needlelike tubular body lumen in a manner extending in an axial direction, and inserted into the patient's body; (b) a needlelike tubular body made of a flexible thin tube having an interior hole through which specified reagent can flow, the needlelike tubular body inserted into the needlelike tubular body lumen of the main tube in a manner movable in the axial direction, and its tip section projected outward from a projection hole provided in a distal section of the main tube to puncture specified tissue in the patient's body, in order to inject the reagent into the body tissue through the interior hole; (c) a first guide wire insertion tube having flexibility, positioned in a manner extending in the axial direction along a side face of the main tube in its distal section and integrated, and having in its interior a first guide wire lumen whose opening on distal side and opening on proximal side open in a manner sandwiching the projection hole; (d) a first guide wire inserted into the first guide wire lumen in the first guide wire insertion tube in a manner movable in the axial direction; (e) a second guide wire insertion tube having flexibility, positioned in a manner extending in the axial direction along the side face of the main tube in its distal section and integrated, and having in its interior a second guide wire lumen whose opening on distal side and opening on proximal side open with a specified distance provided in between in the axial direction on a proximal side of the projection hole; (f) a second guide wire inserted into the second guide wire lumen in the second guide wire insertion tube in a manner movable in the axial direction; and (g) a support tube having flexibility and having a tip section provided as a free end, the support tube provided in a manner branching and extending from the main tube, and having in its interior a continuous lumen that continues to the second guide wire lumen through the opening on distal side in the second guide wire lumen, wherein a part of the second guide wire extending from the opening on distal side in the second guide wire lumen is inserted into the continuous lumen in a manner movable in the axial direction.

In the aforementioned embodiment, the reactive force of puncturing can also be received in a reliable and sufficient manner by the first guide wire, second guide wire and support tube, or further by the plane formed by the two guide wires.

As a result, the main tube is stably positioned inside such as the blood vessel and a specified position in body tissue can be punctured smoothly to a specified depth. Since the balloon and balloon lumen are no longer necessary, a greater part of the main tube, except for the distal section, only has a needlelike tubular body lumen. Therefore, the diameter or size of the main tube can be reduced in an advantageous manner.

In this embodiment, therefore, the main tube or the entire apparatus can also be smoothly inserted into the patient's body in an advantageous manner, and accurate injection of reagent into a lesion or other part of body tissue can be achieved easily and reliably.

In this embodiment, one area of particular interest is that the first guide wire insertion tube and second guide wire insertion tube are positioned in a manner extending in the axial direction with respect to the side face of the main tube in the distal section, and integrated in this condition, thus providing the first guide wire lumen and second guide wire lumen in the distal section of the main tube. Therefore, the main tube, first guide wire insertion tube and second guide wire insertion tube can have a multi-layer structure in which each tube comprises multiple layers made of different types of resin, or each tube can have a single-layer structure in any part of the tube, thereby making it easy to comprise respective tubes based on different structures, unlike in cases where the main tube is formed by means of extrusion molding, etc., with multiple lumens provided in its interior. Therefore, it is easy to change the characteristics (such as sliding resistance) of the interior surfaces of the first guide wire lumen, second guide wire lumen and needlelike tubular body lumen individually for each lumen, or to change in a desired manner the characteristics (such as rigidity) of the respective sections where each lumen formed.

In this embodiment, the entire part of one lumen is accommodated in each tube. For this reason, each lumen can be formed very easily without requiring any cumbersome positioning operation to ensure interconnection of the lumens, unlike in situations where, for example, the main tube is formed with multiple split tubes, each containing a part of each lumen must be aligned in the axial direction, and butt-joined with one another to form multiple lumens connected in succession in the axial direction in the interior of the main tube.

Therefore, according to this embodiment a structure, in which the three lumens including the first guide wire lumen, second guide wire lumen and needlelike tubular body lumen are formed very easily with respect to the main tube, can be achieved in an advantageous manner. Also, advancing and retract (movement in the axial direction) of each guide wire or needlelike tubular body in each lumen and advancing and retract of the main tube through tubular organs in the patient's body can be performed more smoothly and effectively by changing the characteristics of the interior surface of each lumen or characteristics of the respective sections where each lumen formed.

3) In Embodiment (1) or (2) described above, the opening on proximal side in the first guide wire lumen is positioned on a proximal side of the opening on distal side in the second guide wire lumen, so that the needlelike tubular body lumen, first guide wire lumen and second guide wire lumen are formed in parallel with one another. In this embodiment, the plane formed by the first guide wire and second guide wire can be ensured in a stable manner. Therefore, the reactive force of puncturing can be received in a more reliable and sufficient manner. As a result, a specified position in body tissue can be punctured to a desired depth in a smoother manner using the tip of the needlelike tubular body.

4) In Embodiment (3) described above, a section in which the needlelike tubular body lumen, first guide wire lumen and second guide wire lumen are placed in parallel with one another is at least 10 mm long. In this embodiment, the plane formed by the first guide wire and second guide wire can be ensured in a more stable manner. Accordingly, smooth puncturing operation can be achieved more effectively.

5) In any one of Embodiments (1) to (4) described above, the second guide wire lumen is at least 20 mm long. This embodiment ensures a sufficient insertion length of the second guide wire into the second guide wire lumen. Accordingly, the second guide wire and support tube are inserted into a tubular organ branching from another tubular organ in which the main tube and first guide wire are inserted, and therefore the second guide wire can be prevented in an advantageous manner from coming off of the second guide wire lumen when the second guide wire is advanced or retracted at a relatively large stroke.

According to this embodiment, in the aforementioned condition the second guide wire can be advanced or retracted in the second guide wire lumen while maintaining a relatively small curvature. This prevents the pressure force of the second guide wire from concentrating on one part of the interior wall surface around the branching part of the support tube inside the main tube, particularly when the second guide wire is advanced. As a result, flexing deformation of the main tube due to the pressure force exerted by the second guide wire onto the interior wall surface of the main tube can be prevented in an effective manner. Accordingly, smooth insertion operation of the main tube into the tubular organ can be achieved in a stable manner.

6) In any one of Embodiments (1) to (5) described above, the total length of the second guide wire lumen and continuous lumen is 200 mm or less. In this embodiment, the second guide wire lumen can be dimensioned to approximately equivalent to or shorter than the length from the heart to the aortic arch in order to virtually prevent the second guide wire lumen from flexing along the aortic arch, when, for example, reagent is injected into the cardiac muscle. As a result, sliding resistance during advancing or retracting of the second guide wire in the second guide wire lumen can be reduced in an advantageous manner, and consequently smooth advancing and retracting of the second guide wire, or smooth injection of reagent into the cardiac muscle, can be achieved in an advantageous manner.

7) In any one of Embodiments (1) to (6) described above, the opening on proximal side in the first guide wire lumen is positioned on a distal side of the opening on proximal side in the second guide wire lumen.

As mentioned above, the second guide wire is advanced and retracted at a relatively large stroke in the second guide wire lumen, and thus the second guide wire lumen should desirably have a certain length in order to prevent the second guide wire from falling out from the second guide wire lumen. On the other hand, the first guide wire is advanced and retracted at a relatively small stroke in the first guide wire lumen. Therefore, the first guide wire lumen need not be as long as the second guide wire lumen. Accordingly, this embodiment prevents the first guide wire lumen from becoming unnecessarily longer than the second guide wire lumen. This, in turn, contributes significantly to diameter or size reduction of the main tube.

8) In any one of Embodiments (1) to (7) described above, the main tube comprises a multi-layer section in which an inner resin layer is laminated with an external resin layer having characteristics different from those of the inner resin layer. In this embodiment, it is possible, for example, to easily change the sliding resistance and other characteristics of the needlelike tubular body with respect to the interior surface of the needlelike tubular body lumen, or partially change the rigidity and other characteristics of the main tube. Therefore, smooth advancing and retracting of the needlelike tubular body, smooth insertion of the main tube into tubular organs in the patient's body, or smooth injection of reagent, can be achieved in an advantageous manner.

9) In any one of Embodiments (1) to (8) described above, the main tube has a multi-layer structure in which an inner resin layer is laminated on its exterior with a braided reinforcement layer made of resin or metal. This embodiment increases in an advantageous manner the pushability and kink resistance when the main tube is inserted into tubular organs in the patient's body.

10) In any one of Embodiments (1) to (9) described above, the main tube has a structure whereby the flexibility increases from the proximal side toward the distal side gradually or in steps. This embodiment virtually improves the pushability and trackability of the main tube into/to meandering tubular organs in the patient's body.

11) In any one of Embodiments (2) to (10) described above, the first guide wire insertion tube comprises a multi-layer section in which a flexible outer resin layer is laminated with an inner resin layer having small sliding resistance with respect to the first guide wire. This embodiment allows the first guide wire to be advanced and retracted smoothly in the first guide wire lumen. Also, the flexibility of the first guide wire insertion tube prevents the distal section of the main tube from contacting the interior surface of meandering tubular organs in the patient's body when the main tube is inserted into the organs, thereby minimizing damage to the interior surface.

12) In Embodiment (11) described above, a distal end of the first guide wire insertion tube has a single-layer structure comprising only a flexible resin layer. Based on this embodiment, the distal end of the flexible first guide wire insertion tube functions as the tip of the main tube when the main tube is inserted into meandering tubular organs in the patient's body, thereby further minimizing damage to the interior surface of the organs due to contact between the tip of the main tube and the interior surface.

13) In any one of Embodiments (2) to (12) described above, at least a proximal end section of the second guide wire insertion tube has a multi-layer structure in which a flexible outer resin layer is laminated with an inner resin layer having small sliding resistance with respect to the second guide wire. This embodiment allows smoother advancing and retracting of the second guide wire in the second guide wire lumen. Also, the flexibility of the second guide wire insertion tube minimizes damage to the interior surface of tubular organs when the main tube is inserted into the organs, which may otherwise occur due to contact between the distal section of the main tube and the interior surface.

14) In any one of Embodiments (2) to (13) described above, the distal end section of the second guide wire insertion tube has a multi-layer structure in which a flexible resin layer is laminated on its interior or exterior side with a resin layer having rigidity higher than that of the flexible resin layer.

This embodiment prevents in an advantageous manner the flexing deformation tendency of the main tube due to the pressure force exerted by the second guide wire onto the interior wall at the distal end of the second guide wire insertion tube, or specifically onto the interior wall around the branching part of the support tube in the main tube, even if such pressure force is exerted when the second guide wire is advanced in a condition where the second guide wire and support tube are inserted into a tubular organ branching from another tubular organ in which the main tube and first guide wire are inserted. Accordingly, smooth insertion operation of the main tube into the tubular organ can be achieved in a stable manner.

15) In any one of Embodiments (1) to (14) described above, the support tube has a length of 10 to 40 mm. In this embodiment, the support tube has an appropriate length and thus insertion of the support tube into a tubular organ branching from another tubular organ in which the main tube is inserted becomes easily. Also, sufficient supporting force of the second guide wire by the support tube can be ensured in a stable and advantageous manner.

16) In any one of Embodiments (1) to (15) described above, a tip section of the support tube provided as a free end has higher flexibility than the base section. This embodiment minimizes damage to the interior surface of tubular organs when the support tube is inserted into the organs, which may otherwise occur due to contact between the tip of the support tube and the interior surface. In addition to the aforementioned effect, sufficient supporting force of the second guide wire by the support tube can be ensured because the rigidity of the tip of the support tube is higher than that of the base, Furthermore, the pushability of the support tube into tubular organs also improve.

17) In Embodiment (16) described above, the tip section of the support tube has a single-layer structure comprising only a flexible resin layer, while the base section has a multi-layer structure in which the flexible resin layer is laminated on its interior or exterior side with a resin layer having rigidity higher than that of the flexible resin layer, so that the tip section has higher flexibility than the base section. This embodiment provides in a more reliable manner the effect of preventing damage to the interior surface of tubular organs due to contact between the support tube tip and the interior surface of tubular organs, the effect of improving the supporting force of the second guide wire by the support tube, and also the effect of improving the pushability of the support tube.

18) In any one of Embodiments (1) to (17) described above, a marker made of a radio opaque material is provided in a fixed manner in the distal end section of the support tube. This embodiment allows the support tube position in the patient's body to be identified with ease. This permits easy identification of whether or not the support tube has been inserted in a desired tubular organ, as well as identification of the inserted length and other necessary information. As a result, reagent can be injected in a more appropriate and accurate manner.

19) A method of producing reagent injection apparatus structured to inject reagent into tissues in the patient's body, characterized by comprising: (a) a step of preparing a main tube having flexibility, providing in its interior a needlelike tubular body lumen in a manner extending in an axial direction and allowing a needlelike tubular body for injecting the reagent into the body tissue to be inserted through the needlelike tubular body lumen, and having a projection hole in a distal section for projecting a tip of the needlelike tubular body from the needlelike tubular body lumen; (b) a step of preparing a first guide wire insertion tube having flexibility and providing in its interior a first guide wire lumen for inserting a first guide wire in a manner extending in an axial direction; (c) a step of integrating the first guide wire insertion tube with the distal section of the main tube in a condition where openings on distal side and proximal side in the first guide wire lumen open in the distal section of the main tube in a manner sandwiching the projection hole; (d) a step of preparing a second guide wire insertion tube having flexibility and providing in its interior a second guide wire lumen for inserting a second guide wire in a manner extending in an axial direction; (e) a step of integrating the second guide wire insertion tube with the distal section of the main tube in a condition where openings on distal side and proximal side in the second guide wire lumen open in the distal section of the main tube in a manner keeping a specified distance in between in the axial direction on a proximal side of the projection hole; (f) a step of preparing a support tube having flexibility and providing in its interior a continuous lumen for inserting the second guide wire projecting from the opening on distal side in the second guide wire lumen; and (g) a step of positioning the continuous lumen so that it continues to the second guide wire lumen through the opening on distal side in the second guide wire lumen, and also integrating a base of the support tube with a distal end of the second guide wire insertion tube in a condition where a tip of the support tube remains a free end and in a manner allowing the support tube to branch from the main tube.

In this embodiment, the main tube, first guide wire insertion tube and second guide wire insertion tube are integrated, with each tube having one lumen in its interior and made of a separate member independent of one another, in order to form the needlelike tubular body lumen, first guide wire lumen and second guide wire lumen inside the apparatus. For this reason, each tube can have a multi-layer structure in which the tube comprises multiple layers made of different types of resin, or each tube can have a single-layer structure in any part of the tube, thereby making it easy and cost effective to comprise respective tubes based on different structures, unlike in cases where the main tube is formed by means of extrusion molding, etc., with the needlelike tubular body lumen, first guide wire lumen and second guide wire lumen formed simultaneously. Because of this, it is easy to change the characteristics (such as sliding resistance) of the interior surfaces of the first guide wire lumen, second guide wire lumen and needlelike tubular body lumen individually for each lumen, or to change in a desired manner the characteristics (such as rigidity) of the respective sections where each lumen formed.

In this embodiment, the first guide wire insertion tube and second guide wire insertion tube are integrated on the side face of the main tube. Because of this, each lumen can be formed very easily with respect to the main tube, without requiring any cumbersome positioning operation to ensure interconnection of the lumens, unlike in situations where, for example, the main tube is formed with multiple split tubes, each containing a part of each lumen must be aligned in the axial direction, and butt-joined with one another to form multiple lumens continuing in the axial direction in the interior of the apparatus.

A reagent injection apparatus formed in accordance with this embodiment allows the reactive force of puncturing to be received in a reliable and sufficient manner by the first guide wire, second guide wire and support tube, or further by the plane formed by the two guide wires. As a result, the main tube is stably positioned inside such as a blood vessel and a specified position in body tissue can be punctured smoothly to a specified depth. Also, the balloon and balloon lumen are no longer necessary. Furthermore, a greater part of the main tube, except for the distal section, only has a needlelike tubular body lumen. Therefore, the diameter or size of the main tube can be reduced in an advantageous manner.

For the reasons explained above, this embodiment allows for production in a very easy and inexpensive manner a reagent injection apparatus that virtually enables advancing and retracting of each guide wire or needlelike tubular body in each lumen or smooth insertion of the main tube into tubular organs in the patient's body, and such reagent injection apparatus also achieves accurate and reliable injection of reagent in a desired part of body tissue.

The following sections explain in details and by using figures the structure of how a reagent injection apparatus conforming to the embodiments can be applied, in order to more specifically describe the embodiments.

Figure 2:
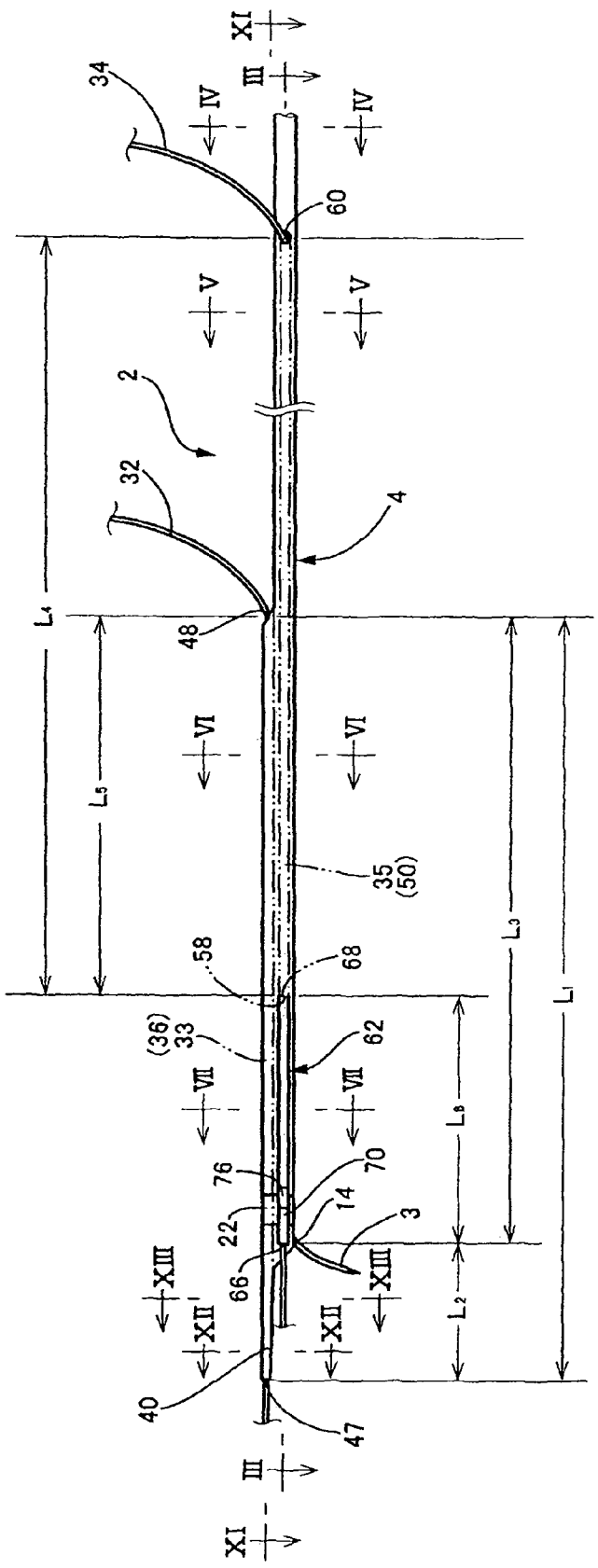
FIG. 2 is an explanatory drawing presenting a partially enlarged view of FIG. 1.

First, FIGS. 1 and 2 show the general view and key part, respectively, of a reagent injection catheter used to inject reagent into lesions in the cardiac muscle, presenting an example of reagent injection apparatus having a structure conforming to the embodiments. In FIGS. 1 and 2, numeral 2 represents a main tube comprising a tubular body having appropriate thickness and length (1,300-1,500 mm, for example) permitting insertion into the blood vessels extending from the thigh or wrist to the heart of the patient's body, over the entire length of the blood vessels. This main tube 2 has a needlelike tubular body 3 inserted in a manner movable in the axial direction.

This main tube 2 has a distal section 4 corresponding to the forward end in the insertion direction into human blood vessels (left side in FIG. 1), and a proximal section 6 corresponding to the rearward end in the insertion direction into human blood vessels (right side in FIG. 1). The section between these distal section 4 and proximal section 6 provides an intermediate section 8. Here, the distal section 4 refers to the distance between an opening on distal side 47 and an opening on proximal side 60 described later (210 mm in this embodiment). Although the boundary between the intermediate section 8 and the proximal section 6 is formed by resin materials being used having only different flexibility and indistinct, it refers to the distance up to about 900 mm from a proximal end (a tip of a socket 12) of the main tube 2. The intermediate section 8 refers to the part except for the distal section 4 and the proximal section 6. To facilitate easy understanding of the structure of the main tube 2 and overall reagent injection catheter, the side of the main tube 2 where the distal section 4 is located shall be hereinafter referred to as the distal side or front side, while the side where the proximal section 6 is located shall be hereinafter referred to as the proximal side or rear side.

Figure 3:
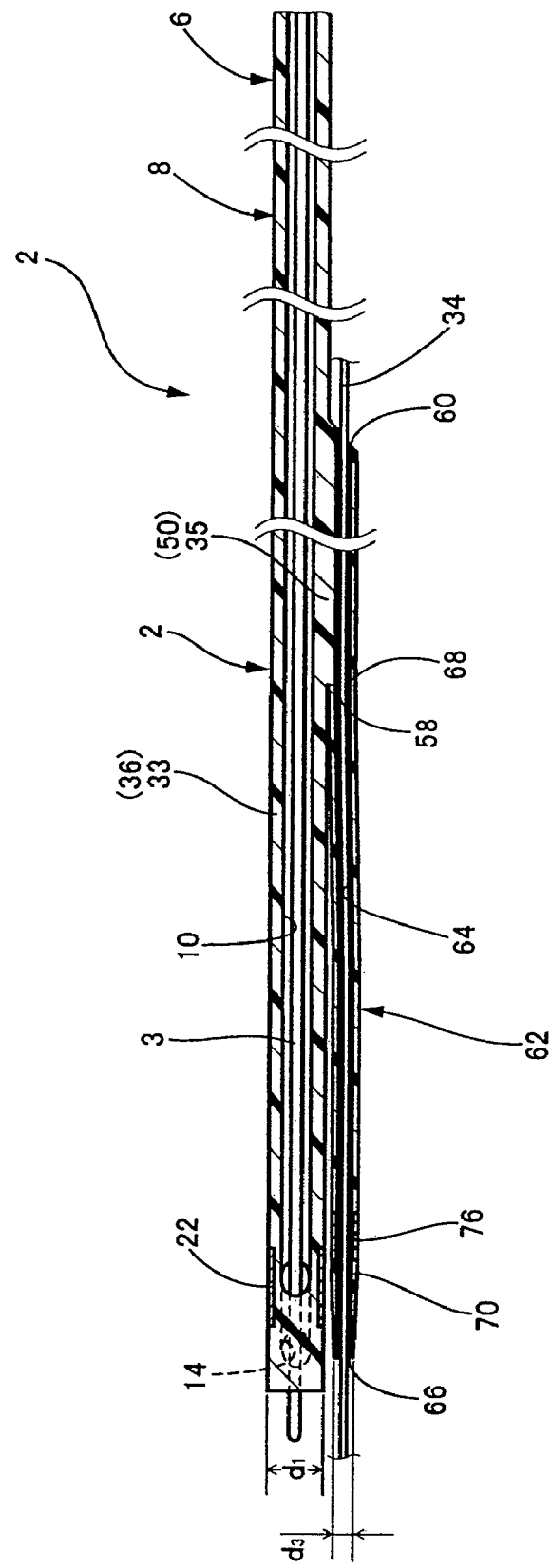
FIG. 3 is an explanatory drawing showing section III-III of FIG. 2.
Figure 4:
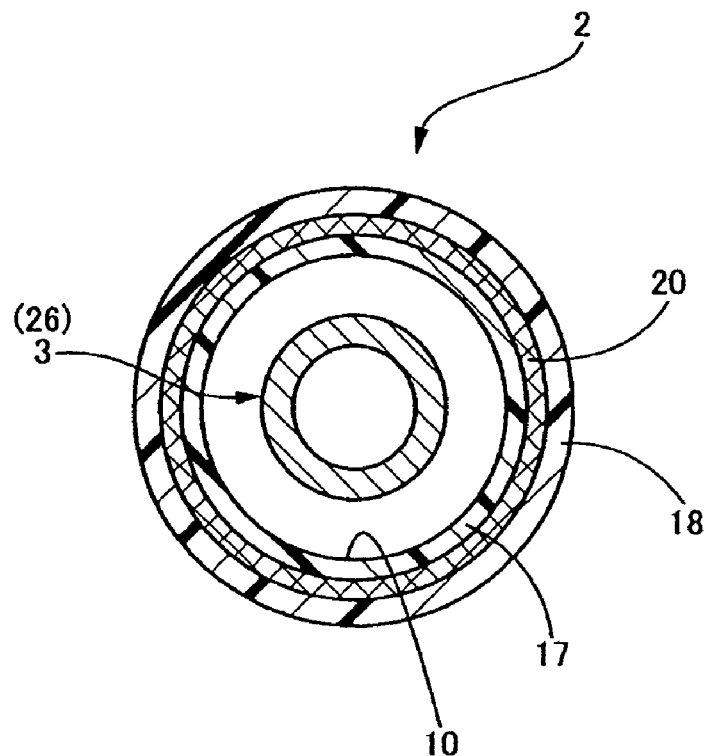
FIG. 4 is an explanatory drawing showing an enlarged view of section IV-IV of FIG. 2.

As shown in FIG. 3, a needlelike tubular body lumen 10, in which the needlelike tubular body 3 is inserted in a manner movable in the axial direction, is formed inside the main tube 2 over roughly the entire length of the tube and in a manner extending continuously in the axial direction. This needlelike tubular body lumen 10 opens rearward through an interior hole in a socket 12 connected to the proximal end of the proximal section 6 of the main tube 2 (refer to FIG. 1). The needlelike tubular body lumen 10 also opens downward at the distal end of the distal section 4, through a projection hole 14 provided in the tube wall surface below the distal end. This projection hole 14 is positioned in such a way that its center O is positioned in the plane α that includes the center axis $P_0$ of the main tube 2 and center axis $P_1$ of the needlelike tubular body lumen 10 (refer to FIG. 6). The outer diameter of the main tube 2 (the dimension indicated by $d_1$ in FIG. 3) is set to approx. 1.1 mm, for example. The inner diameter of the needlelike tubular body lumen 10 is set to approx. 0.69 mm, for example.

As shown in FIGS. 4 through 7, in this embodiment the main tube 2 comprises a flexible resin tube partially having a multi-layer structure in a cross-section view. In other words, the distal end section of the distal section 4 of the main tube 2 has a single-layer structure comprising only one type of flexible resin layer formed by flexible polyamide resin (this structure is not illustrated). Then, all of the remainder of the main tube 2, except for the distal end section comprising a single-layer structure based on flexible resin layer, has a multi-layer structure in which an inner resin layer 17 and outer resin layer 18 are integrally laminated on top of each other. This inner resin layer 17 is formed by, for example, PTFE resin offering excellent sliding property. The outer resin layer 18 is formed by flexible polyamide resin. Furthermore, the main tube 2 has a reinforcement layer 20, constituted by braided thin stainless metal wires, positioned at the lamination layer between the inner resin layer 17 and outer resin layer 18.

With the main tube 2, therefore, the interior surface of the needlelike tubular body lumen 10 comprises the inner resin layer 17, and thus the sliding resistance is kept small with respect to the needlelike tubular body 3 inserted into the needlelike tubular body lumen 10, while attachment of blood clot can be prevented in an advantageous manner. Based on the flexibility of the outer resin layer 18, trackability to meandering blood vessels in the patient's body is also increased in an advantageous manner. Furthermore, presence of the reinforcement layer 20 comprising braided stainless wires increases in an advantageous manner the pushability into human blood vessels, the torquability that is the transmission characteristics of rotational torque, and the kink resistance to inhibit bending deformation of the needlelike tubular body lumen 10 due to twisting or flexing of the main tube 2. In addition, the structure of the distal end section where only a flexible resin layer is provided prevents the interior surface of human blood vessels from being damaged by contact with the distal end of the main tube 2 when the main tube is inserted into the blood vessels.

The structure of the main tube 2 is not at all limited to the one described above, as long as flexibility can be ensured. For example, the entire main tube 2 can comprise a single-layer resin tube made of a single resin layer, or it can comprise a multi-layer resin tube having multiple types of resin layers laminated on top of each other. Or, the main tube 2 can also be constituted by a metal or composite tube formed by Ni—Ti alloy or any other superelastic alloy material, or stainless or any other metal material, used individually or in combination of any resin material, etc. Furthermore, the resin layer of the main tube 2 can also use polyethylene resin, in place of, or along with, the resin material illustrated above. Moreover, the reinforcement layer 20 can also be formed by braided thin metal wires of Ni—Ti alloy and other superelastic alloy materials or braided synthetic resin fibers, among others, in addition to stainless.

Here, the outer resin layers 18 of the distal section 4, intermediate section 8 and proximal section 6 of the main tube 2 use polyamide resins of different types having different levels of flexibility, respectively. Specifically, the outer resin layer 18 of the distal section 4 is formed by a type of polyamide resin having greater flexibility than the outer resin layer 18 of the intermediate section 8, while the outer resin layer 18 of the intermediate section 8 is formed by another type of polyamide resin having greater flexibility than the outer resin layer 18 of the proximal section 6. This way, the flexibility of the main tube 2 gradually increases from the proximal side toward the distal side. As a result, the pushability of the main tube 2 into blood vessels can be enhanced in an advantageous manner, along with the torquability of rotational torque and other properties, so that the main tube 2 can be inserted more smoothly into these meandering blood vessels.

As shown in FIGS. 2 and 3, the main tube 2 has a marker tube 22 affixed in the immediate vicinity of the proximal side of the projection hole 14 in the distal section 4. This marker tube 22 is formed, for example, by a radio opaque material such as gold, platinum or platinum rhodium alloy. This way, when the main tube 2 is inserted into blood vessels the position of the marker tube 22 affixed in the immediate vicinity of the projection hole 14 in the main tube 2 can be identified by X-ray fluoroscopy. This permits easy identification of the position of the projection hole 14 inside blood vessels.

Figure 8:
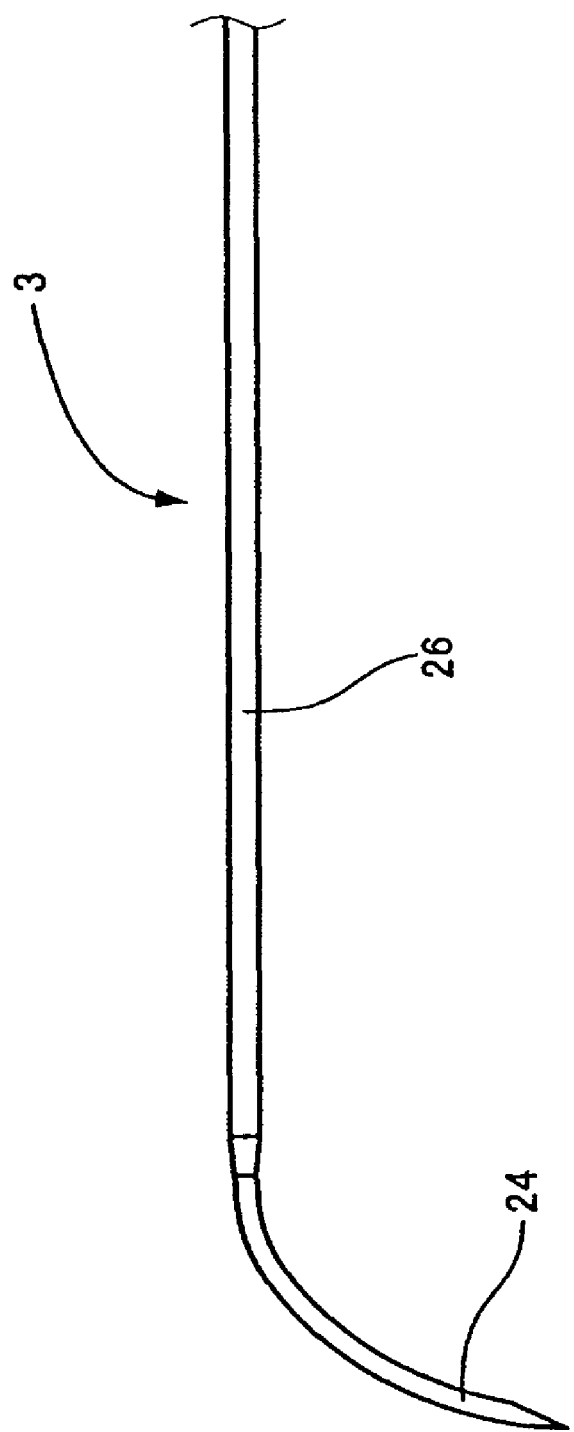
FIG. 8 is an eront view showing the needlelike tubular body used in the reagent injection apparatus shown in FIG. 1.

On the other hand, the needlelike tubular body 3 inserted into the needlelike tubular body lumen 10 in the main tube 2 comprises a flexible thin tube over its entirety, as shown in FIG. 8. And, its tip (distal end) provides a sharp needle 24. The part excluding this tip providing the needle 24 forms a reagent passage tube 26 comprising a thin tube longer than the main tube 2. Here, the outer diameter of the needle 24 is set to approx. 0.4 mm, for example. On the other hand, the outer diameter of the reagent passage tube 26 is set to approx. 0.56 mm, for example.

As evident from FIG. 1, the needlelike tubular body 3 has a connector 28 attached at the end (proximal end) of the reagent passage tube 26. Furthermore, this connector 28 is connected to a syringe 30. Through this syringe 30, specified reagent, such as one containing any osteoblast or growth factor to regenerate the cardiac muscle tissue that has virtually become necrotic, or specifically bFGF (basic fibroblast growth factor), VEGF (vascular endothelial growth factor), or HGF (hepatocyte growth factor), is introduced into the reagent passage tube 26 and discharged to outside from the opening in the needle 24 at the tip.

This reagent passage tube 26 in the needlelike tubular body 3 as mentioned above is formed by, for example, flexible synthetic resin materials such as polytetrafluoroethylene (PTFE) resin and polyimide resin. On the other hand, the needle 24 is formed by elastic materials such as Ni—Ti alloy and other superelastic alloy materials, or stainless and other metal materials. This way, the needlelike tubular body 3 exhibits sufficient flexibility or elasticity and thus is inserted easily into the needlelike tubular body lumen 10 in the main tube 2 that has been inserted into blood vessels, in conformance with the bending and meandering blood vessels, thereby permitting smooth advancing and retracting in the axial direction.

Figure 9:
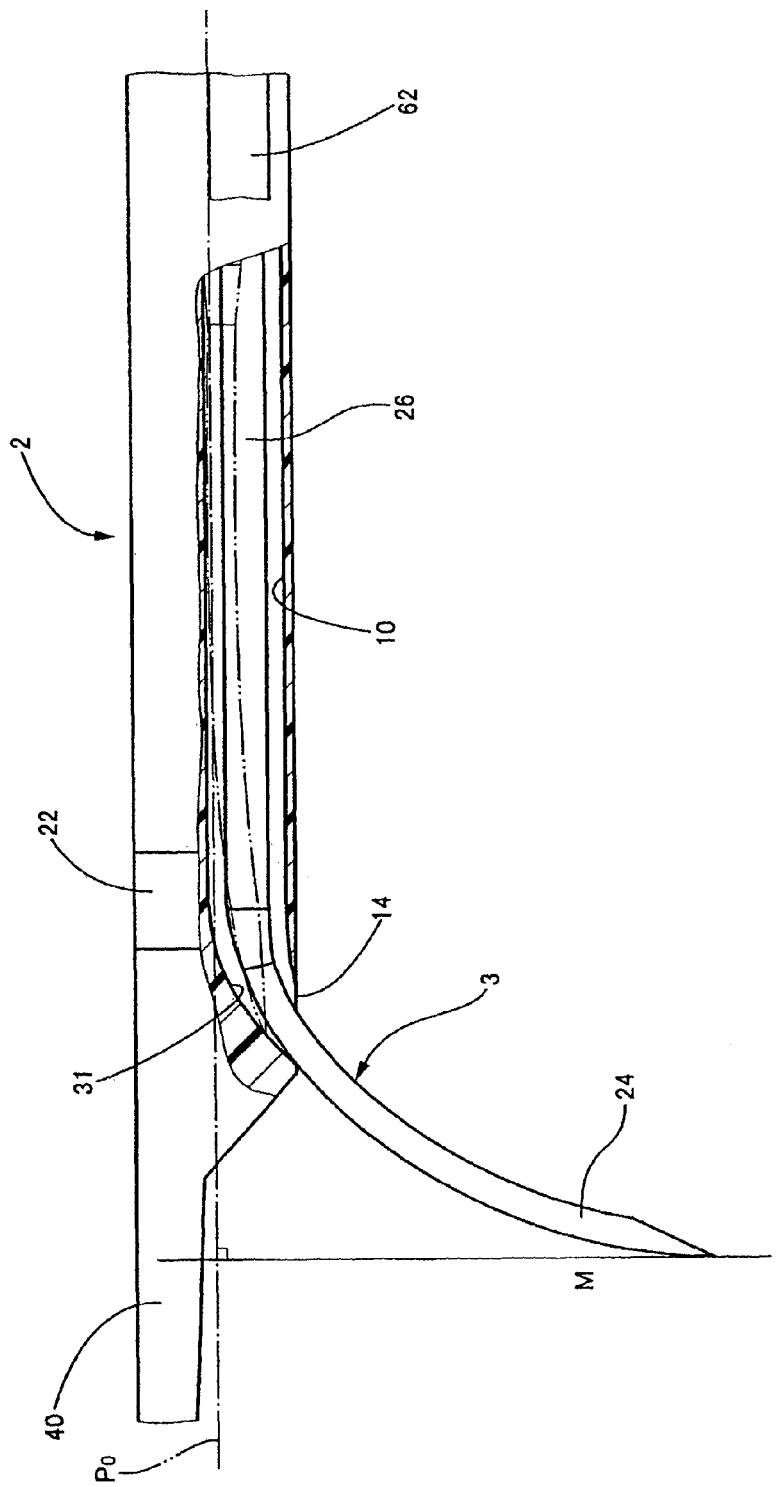
FIG. 9 is an explanatory drawing including a partial cutout view, presenting a partially enlarged view of the reagent injection apparatus shown in FIG. 1.

As shown in FIG. 9, the inner periphery of the distal end section of the needlelike tubular body lumen 10 is formed as a guide surface 31 comprising a convex curved surface that curves forward in the opening direction of the projection hole 14. Also, the needle 24 of the needlelike tubular body 3 also has a curved shape corresponding to the curved shape of the guide surface 31. As a result, when the needle 24 reaches the section of the main tube 10 where the projection hole 14 is formed, as a result of advancing movement of the needlelike tubular body 3 in the needlelike tubular body lumen 10, then this needle 24 is guided smoothly toward the projection hole 14 by the guide surface 31. Thereafter, further advancing of the needlelike tubular body 3 causes the needle 24 to project from the projection hole 14, and this projection also causes the needle 24 to puncture the cardiac muscle.

The curved shape of the guide surface 31 of the needlelike tubular body lumen 10 or that of the needle 24 can be determined as deemed appropriate in consideration of the rigidity and other characteristics of the needle 24, for example. Although the degree of radius of curvature and other characteristics of the curved section of such guide surface 31 or needle 24 are not at all limited, it is desirable that, when the curved form of the guide surface 31 is combined with the curved shape of the needle 24 and the needle 24 is projected from the projection hole 14, the projection angle θ at the contact point of both should become approx. 45° or greater.

Figure 10:
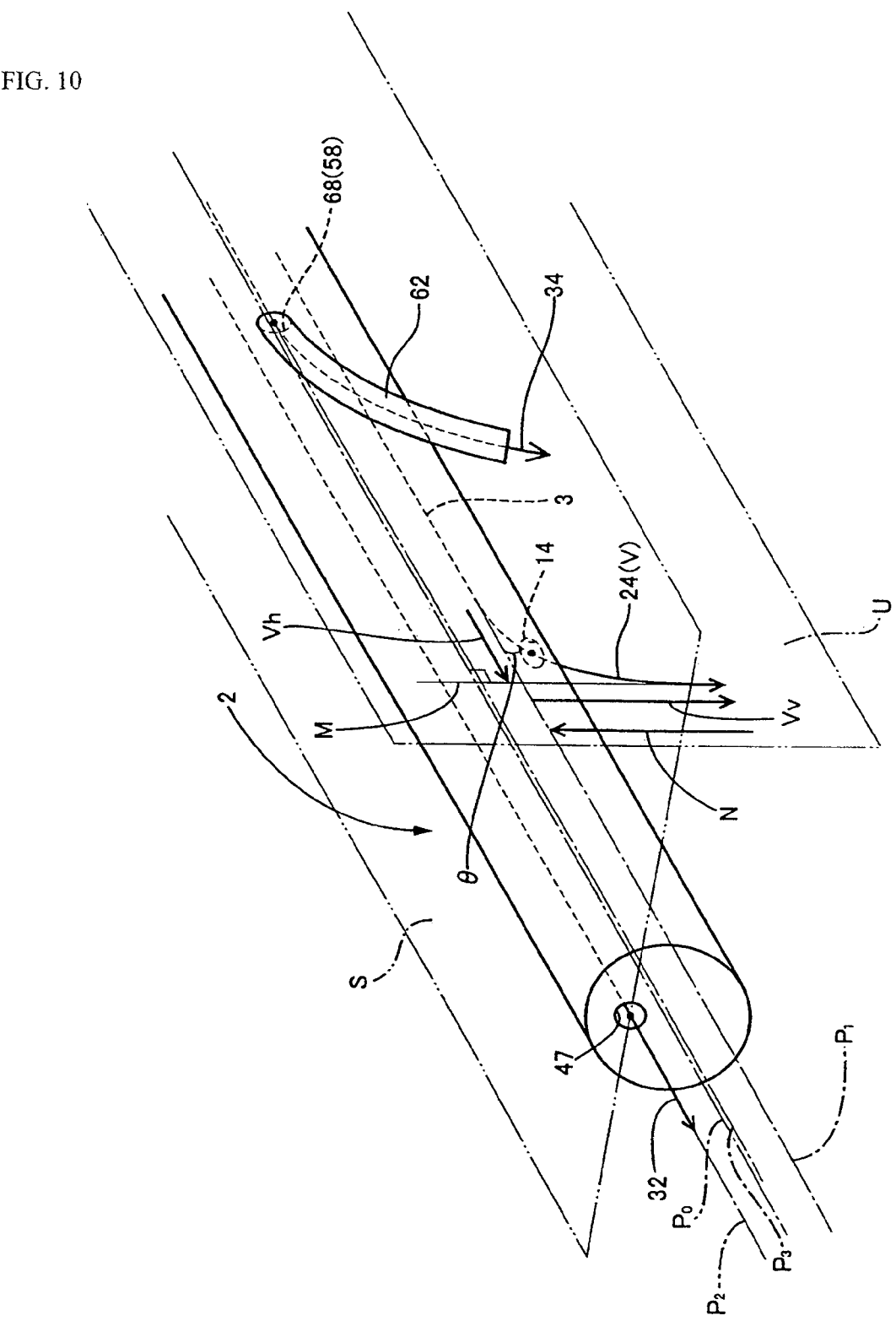
FIG. 10 is an explanatory drawing providing a schematic illustration of the reagent injection apparatus shown in FIG. 1.

This way, the tangential line M at the tip can be caused to cross at right angles with the center axis $P_0$ of the main tube 2 at a position closer to the projection hole 14, when the needle 24 is projecting from the projection hole 14, as shown in FIGS. 9 and 10. In this case, a sufficient component force can be ensured that acts in the direction of the needlelike tubular body 3 entering the cardiac muscle (i.e., the size of Vv, of the two vectors Vv and Vh shown in FIG. 10, which runs perpendicularly to the center axis $P_0$ of the main tube 2). As a result, the needle 24 of the needlelike tubular body 3 enters the cardiac muscle more smoothly.

By the way, in this embodiment the distal section 4 of the main tube 2 having the aforementioned structure has a first guide wire insertion section 33 in which a first guide wire 32 is inserted, and a second guide wire insertion section 35 in which a second guide wire 34 is inserted.

Figure 11:
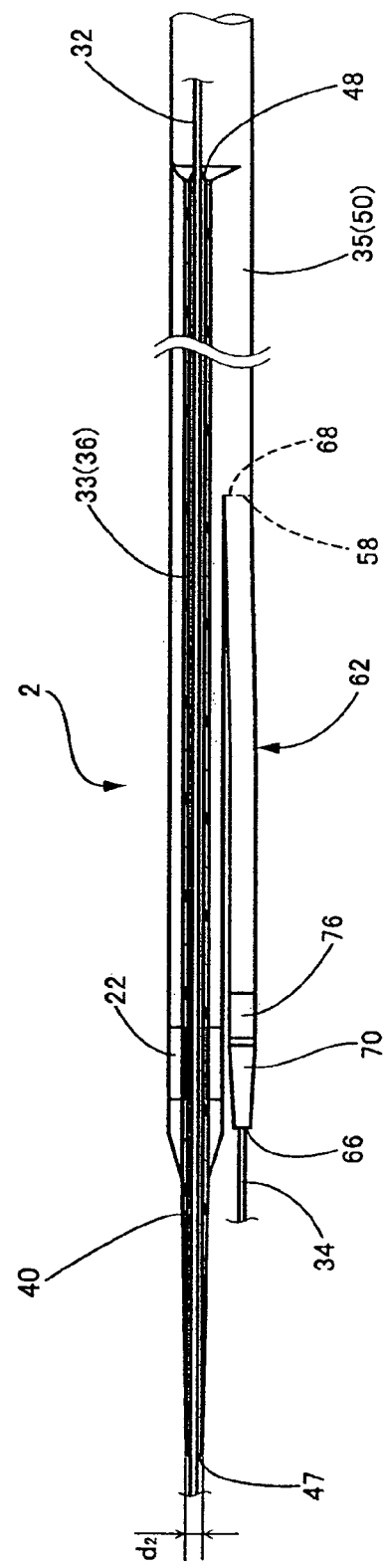
FIG. 11 is an explanatory drawing showing an enlarged view of section XI-XI of FIG. 2.

To be more specific, the first guide wire insertion section 33 shown in FIGS. 2 and 11 is integrated by means of welding, etc., with the top side face of the main tube 2, which is the opposite side of the downward part to which the projection hole 14 opens. Here, the first guide wire insertion tube 36 comprising the first guide wire insertion section 33 extends in the axial direction, and one end in the axial direction projects forward from the distal end of the main tube 2. Also, a first guide wire lumen 38 through which the first guide wire 32 is inserted is provided inside the first guide wire insertion tube 36 in a manner extending continuously in the axial direction over the entire length.

In other words, the first guide wire insertion section 33 has a small-diameter tip projection section 40 that projects forward from the distal end of the distal section 4 of the main tube 2, and is integrally provided with the top side face of the distal section 4 of the main tube 2. And, the first guide wire 32 is inserted into the first guide wire lumen 38 provided in this tip projection section 40 in a manner movable in the axial direction.

The outer diameter of the first guide wire insertion tube 36 comprising the first guide wire insertion section 33 (the outer diameter of the tip projection section 40 indicated by $d_2$ in FIG. 11) is smaller than that of the main tube 2 and is set to approx. 0.65 mm, for example. Also, the length of the first guide wire insertion tube 36 (the dimension indicated by $L_1$ in FIG. 2), or specifically the length of the first guide wire lumen 38, is sufficiently shorter than that of the main tube 2 and is set to approx. 60 mm, for example. Furthermore, the length of the section comprising the tip projection section 40 of the first guide wire insertion tube 36 (the dimension indicated by $L_2$ in FIG. 2) is set to approx. 10 mm, for example. In addition, the inner diameter of the first guide wire lumen 38 is set to approx. 0.42 mm, for example.

Here, the first guide wire insertion tube 36 comprises a flexible resin tube partially having a multi-layer structure just like the main tube 2. Accordingly, the first guide wire insertion section 33 partially has a multi-layer structure, as well.

Figure 12:
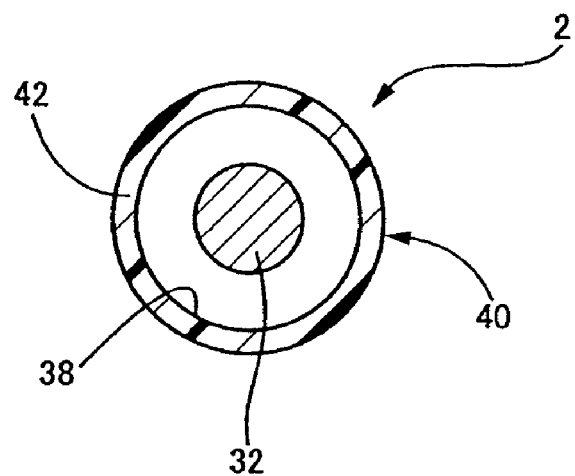
FIG. 12 is an explanatory drawing showing an enlarged view of section XII-XII of FIG. 2.
Figure 13:
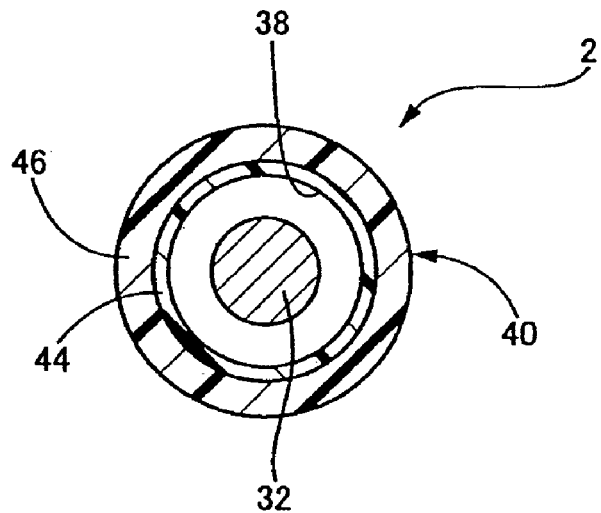
FIG. 13 is an explanatory drawing showing an enlarged view of section XIII-XIII of FIG. 2.
Figure 14:
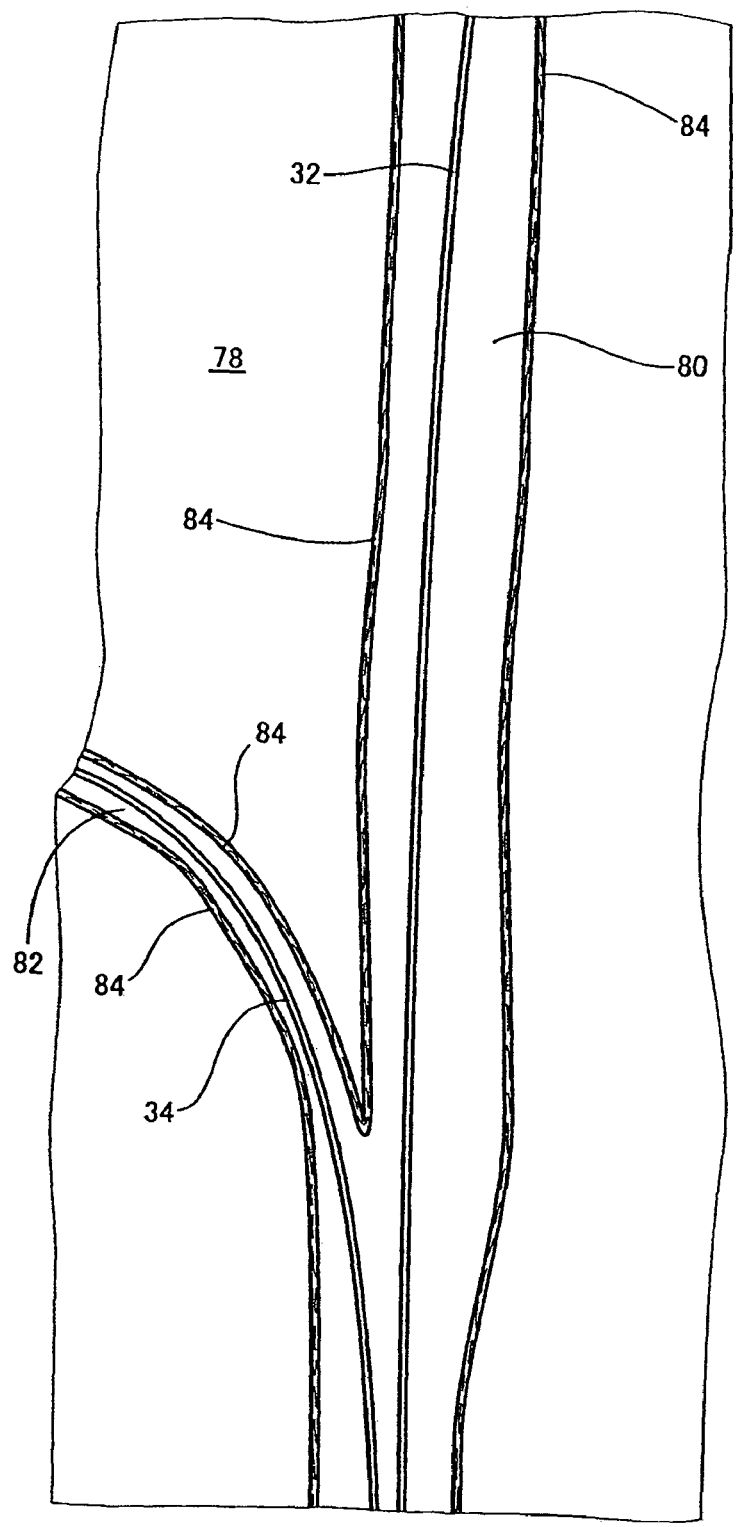
FIG. 14 is an explanatory drawing illustrating an example of operation of injecting specified reagent into a lesion in the cardiac muscle using the reagent injection apparatus shown in FIG. 1.

In other words, the tip of the tip projection section 40 of the first guide wire insertion section 33 has a single-layer structure comprising only one type of flexible resin layer 42 formed by flexible polyamide resin, as shown in FIG. 12. This tip projection section 40 also has an outer periphery of a tapered cylinder shape whose diameter gradually decreases toward the tip, and thus whose thickness also decreases gradually toward the tip (refer to FIG. 11). As shown in FIG. 13, of the first guide wire insertion section 33, all part except for the single-layer tip projection section 40 has a multi-layer structure in which an inner resin layer 44 and outer resin layer 46 are integrally laminated on top of each other. In this embodiment, the inner resin layer 44 is formed, for example, by polyethylene resin offering excellent sliding property. The outer resin layer 46 is formed, for example, by flexible polyamide resin.

This way, the first guide wire insertion section 33 exhibits, at the tip of the tip projection section 40 in an advantageous manner, flexibility that is sufficiently higher than other section. As a result, damage to the interior surface of blood vessels can be prevented when the main tube 2 is inserted into the blood vessels, which may otherwise occur due to contact between the interior surface and the tip projection section 40 of the first guide wire insertion section 33 projecting from the distal end of the main tube 2. Also, since the interior surface of the first guide wire lumen 38 comprises the inner resin layer 44 offering excellent sliding property, the sliding resistance with respect to the first guide wire 32 can be kept small, and thus the first guide wire 32 moves more smoothly inside the first guide wire lumen 38.

By the way, the structure of the first guide wire insertion section 33 is not at all limited to the one described above, and the entire part may have a single-layer structure comprising one type of resin layer, or the entire part may have a multi-layer structure comprising multiple types of resin layers laminated on top of each other. The first guide wire insertion section 33 can also be constituted by a flexible metal or composite tube formed by Ni—Ti alloy or any other superelastic alloy material, or stainless or any other metal material, used individually or in combination of any resin material, etc.

One specific feature of the reagent injection catheter provided by this embodiment is that an opening on distal side 47 in the first guide wire lumen 38 opens toward the distal side at the tip end face of the tip projection section 40 of the first guide wire insertion section 33, as shown in FIG. 2., while an opening on proximal side 48 opens toward the proximal side on side of the intermediate section in the axial direction within the distal section 4 of the main tube 2. In other words, the opening on distal side 47 and opening on proximal side 48 in the first guide wire lumen 38 are positioned in a manner sandwiching the projection hole 14 in the main tube 2.

Figure 6:
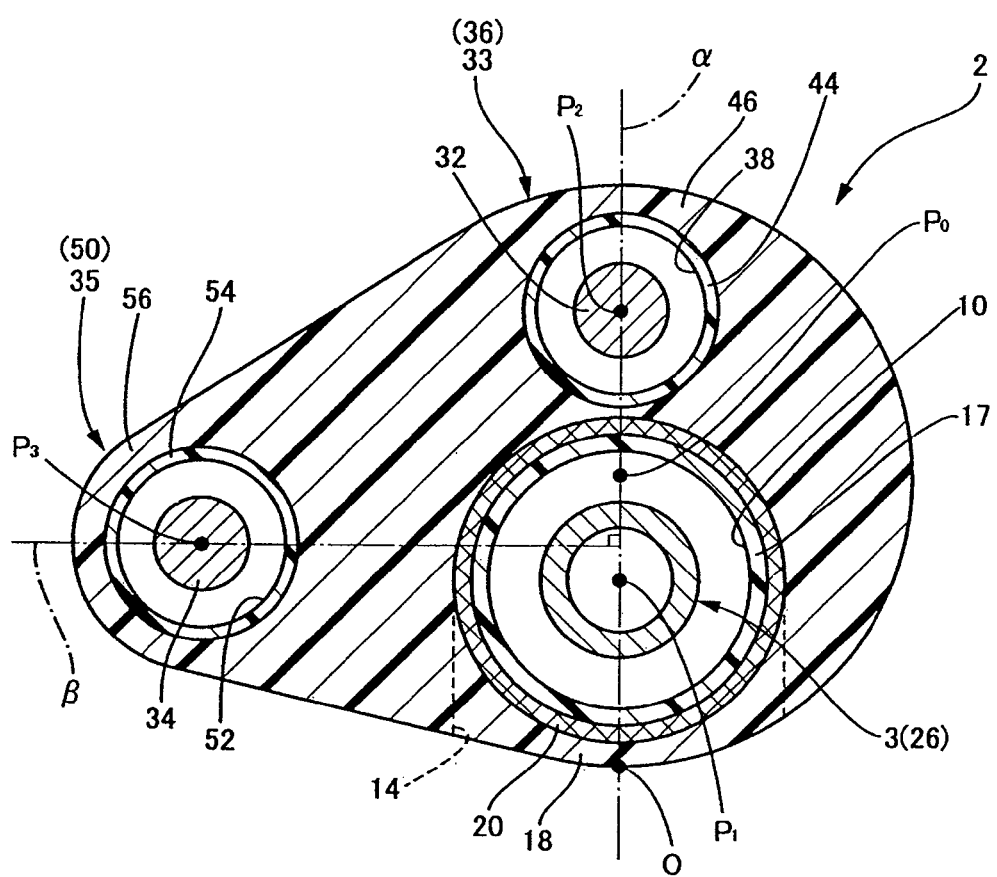
FIG. 6 is an explanatory drawing showing an enlarged view of section VI-VI of FIG. 2.

In other words, the first guide wire lumen 38 extends by specified dimensions toward the distal side and proximal side of the projection hole 14, respectively. As shown in FIG. 6, the section of the first guide wire lumen 38 extending toward the proximal side is positioned directly above the needlelike tubular body lumen 10 so that its center axis $P_2$ exists in the plane α that includes the center axis $P_0$ of the main tube 2, center axis $P_1$ of the needlelike tubular body lumen 10, and center O of the projection hole 14, and thus this section is extended in parallel in a manner overlapping with the needlelike tubular body lumen 10. And into this first guide wire lumen 38, the first guide wire 32 is inserted by means of the so-called monorail method, whereby the guide wire extends toward outside from the opening on distal side 47 and opening on proximal side 48.

This way, the first guide wire 32 inserted into the first guide wire lumen 38, and the needlelike tubular body 3 inserted into the needlelike tubular body lumen 10, are positioned in a manner extending in parallel with each other in the section where the first guide wire lumen 38 and needlelike tubular body lumen 10 extend in parallel with each other. And, because the first guide wire lumen 38 is positioned directly above the needlelike tubular body lumen 10, the cross-section area of the section where the first guide wire lumen 38 and needlelike tubular body lumen 10 extend in parallel with each other is kept small. Here, the length of the first guide wire lumen 38 from the position corresponding to the projection hole 14 to the opening on proximal side 48 (the dimension indicated by $L_3$ in FIG. 2), or specifically the length of the section where the first guide wire 32 and needlelike tubular body 3 extend in parallel with each other, is set to approx. 50 mm, for example.

This structure where the first guide wire lumen 38 and needlelike tubular lumen 10 extend in parallel in a manner overlapping with each other prevents the excessive flexing tendency of the tip projection section 40 due to lower rigidity of the tip projection section 40 around the opening on proximal side 48, unlike in a condition where both the openings on distal side and proximal side 47, 48 are provided in the thin tip projection section 40 having a small diameter, without providing any overlapping section, but where the first guide wire lumen 38 is formed only in this tip projection section 40. For this reason, the first guide wire 32 inserted into the first guide wire lumen 38 does not curve or flex unnecessarily, and can be smoothly advanced or retracted through the first guide wire lumen 38.

On the other hand, as shown in FIGS. 2 and 3, the second guide wire insertion section 35 is integrally constituted by means of welding, etc., in a condition where a second guide wire insertion tube 50 extends in the axial direction along the side face of the main tube 2, with respect to the section with a phase difference of 90° to the section where the first guide wire insertion section 33 is formed on the side face of the main tube 2. The length of the second guide wire insertion tube 50 (the dimension indicated by $L_4$ in FIG. 2), or specifically the length of a second guide wire lumen 52, is sufficiently shorter than the main tube 2 and set to approx. 180 mm, for example. Furthermore, the inner diameter of the second guide wire lumen 52 is set to approx. 0.42 mm, for example.

Here, the entire part of the second guide wire insertion tube 50 is made of a flexible resin tube having a multi-layer structure comprising resin layers of partially different types laminated on top of each other, and accordingly the entire part of the second guide wire insertion section 35 also has a multi-layer structure.

Figure 5:
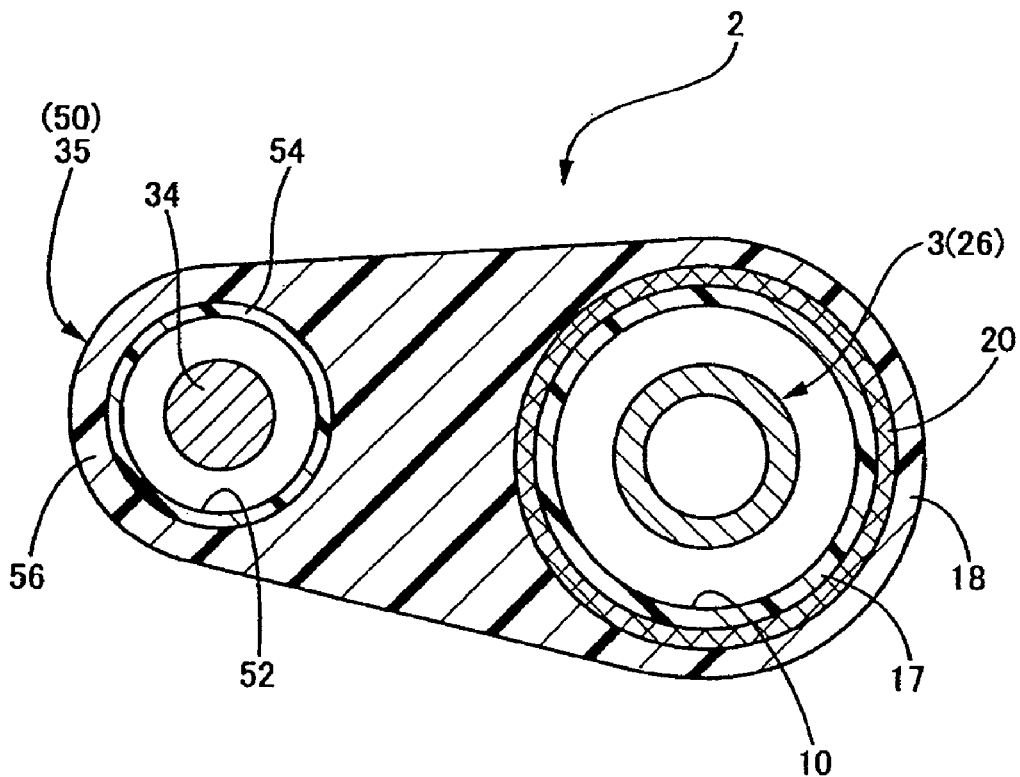
FIG. 5 is an explanatory drawing showing an enlarged view of section ion V-V of FIG. 2.

In other words, the entire part of the second guide wire insertion section 35 has a structure in which an inner resin layer 54 and outer resin layer 56 are integrally laminated on top of each other, as shown in FIGS. 5 and 6. Here, the outer resin layer 56 is formed by the same resin material over the entire length of the second guide wire insertion section 35. The inner resin layer 54 is formed by different resin materials in the distal end section and in the remainder, respectively. Specifically in this embodiment, the outer resin layer 56 is formed by flexible polyamide resin, for example. As for the inner resin layer 54 the distal end section is formed by polyimide resin offering relatively higher rigidity, for example, while the remainder of the layer other than the distal end section is formed by polyethylene resin offering excellent sliding property, for example.

This way, the second guide wire insertion section 35 exhibits sufficient flexibility in the section other than the distal end section. Also, because the sliding resistance of the interior surface of the second guide wire lumen 52 with respect to the second guide wire 34 can be kept small in all section other than the distal end section, the second guide wire 34 moves more smoothly through the second guide wire lumen 52. Furthermore, the rigidity of the distal end section of the second guide wire insertion section 35 is set higher than the rigidity in other section. As a result, the second guide wire insertion section 35, or the main tube 2 with which the second guide wire insertion section 35 is integrated, is prevented from undergoing unnecessary curving or flexing deformation even if, for example, the second guide wire 34 curves or flexes within the distal section of the second guide wire lumen 52 when the second guide wire 34 extends sideward to a support tube 62 with respect to in the axial direction of the main tube 2 and the second guide wire 34 consequently exerts pressure force onto the interior surface of the second guide wire lumen 52.

The structure of the second guide wire insertion section 35 is not at all limited to the one described above, and the entire part may have a single-layer structure comprising one type of resin layer, or the entire part may have a multi-layer structure comprising multiple types of resin layers laminated on top of each other. The second guide wire insertion section 35 can also be constituted by a flexible metal or composite tube formed by Ni—Ti alloy or any other superelastic alloy material, or stainless or any other metal material, used individually or in combination of any resin material, etc.

One specific feature of this embodiment is that, as shown in FIGS. 2 and 3, an opening on distal side 58 in the second guide wire lumen 52 opens toward the distal side in a position on the proximal side of the projection hole 14 within the distal section 4 of the main tube 2, and also on the distal side of the opening on proximal side 48 in the first guide wire lumen 38. An opening on proximal side 60 opens toward the proximal side in the proximal end section within the distal section 4 of the main tube 2, located on the proximal side of the opening on proximal side 48 in the first guide wire lumen 38. In other words, the opening on distal side 58 and opening on proximal side 60 in the second guide wire lumen 52 are provided on the proximal side of the projection hole 14 within the distal section 4 of the main tube 2, in a manner keeping a specified distance in between and sandwiching the opening on proximal side 48 in the first guide wire lumen 38.

Accordingly in the reagent injection catheter provided by this embodiment, the first guide wire lumen 38, second guide wire lumen 52 and needlelike tubular body lumen 10 are extending side by side in parallel in a manner overlapping with each other, in a section where these lumens are positioned between the opening on proximal side 48 in the first guide wire lumen 38 and the opening on distal side 58 in the second guide wire lumen 52, within the distal section 4 of the main tube 2. As shown in FIG. 6, in the section where the first guide wire lumen 38, second guide wire lumen 52 and needlelike tubular body lumen 10 overlap, the second guide wire lumen 52 is positioned on side of the first guide wire lumen 38 and needlelike tubular body lumen 10, so that its center axis $P_3$ exists in the plane $\beta$ perpendicular to the plane $\alpha$ that includes the center axis $P_2$ of the first guide wire lumen 38, center axis $P_1$ of the needlelike tubular body lumen 10, and center O of the projection hole 14.

This way, the second guide wire 34 is inserted into the second guide wire lumen 52 by means of the so-called monorail method, whereby the guide wire extends outside from both the opening on distal side 58 and opening on proximal side 60. And in this condition, the second guide wire 34 is positioned on side of the first guide wire 32 and needlelike tubular body 3 within the intermediate portion of the distal section 4 of the main tube 2 in the axial direction, in parallel with the first guide wire 32 and needlelike tubular body 3 over a specified length.

Here, the length of the second guide wire lumen 52 from the opening on distal side 58 to the position corresponding to the opening on proximal side 48 in the first guide wire lumen 38 (the dimension indicated by $L_5$ in FIG. 2), or specifically the length of the second guide wire lumen 52 in the section where it extends in parallel with the first guide wire lumen 38 and needlelike tubular body lumen 10, is set to approx. 30 mm, for example.

In the reagent injection catheter provided by this embodiment, the support tube 62 is integrally formed with the second guide wire insertion section 35, as shown in FIGS. 1 and 2. This support tube 62 comprises a flexible small-diameter resin tube whose entire length (the dimension indicated by $L_6$ in FIG. 2) is the same as the length from the opening on distal side 58 of the second guide wire lumen 38 to the projection hole 14 and set to approx. 20 mm, for example, and whose outer diameter (the dimension indicated by $d_3$ in FIG. 3) is set to approx. 0.6 mm, for example.

As shown in FIG. 3, a continuous lumen 64 having the same inner diameter (0.42 mm) as the second guide wire lumen 52 is provided inside this support tube 62 in a manner extending continuously in the axial direction over the entire length. Also, this continuous lumen 64 opens through openings on tip and base sides 66, 68, respectively provided in the end faces on tip side and base side of the support tube 62.

Figure 7:
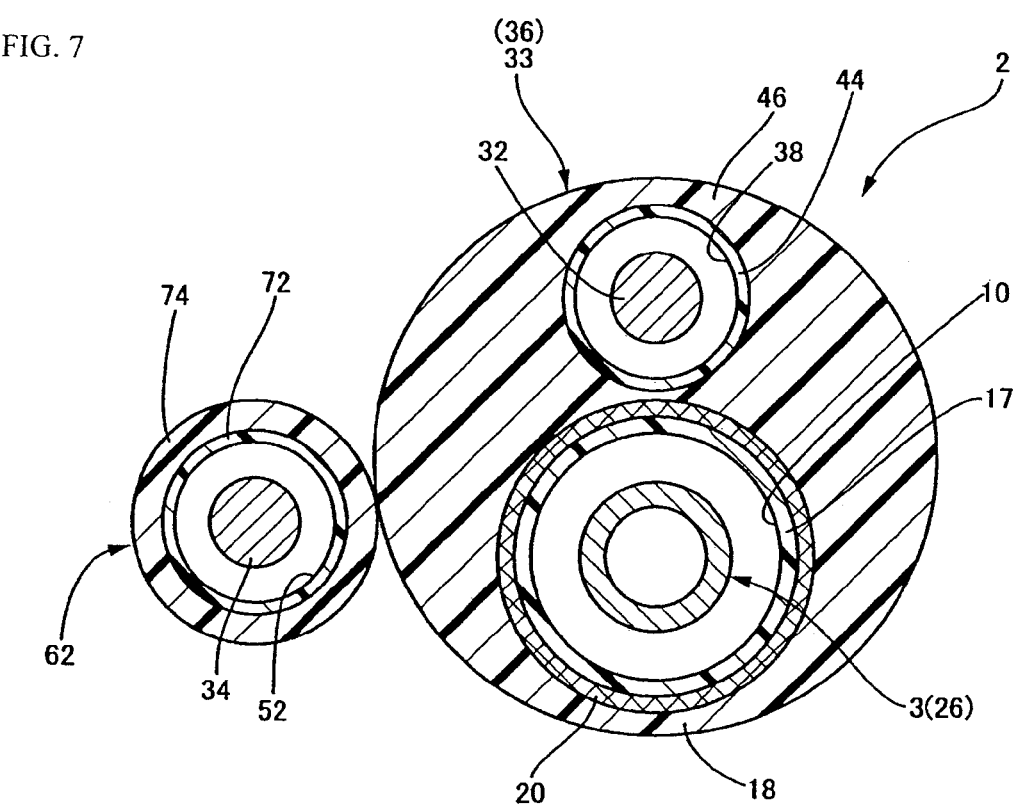
FIG. 7 is an explanatory drawing showing an enlarged view of section VII-VII of FIG. 2.

In addition, a tip section 70 of this support tube 62 adopts a single-layer structure comprising one type of flexible resin formed, for example, by flexible polyamide resin. Also, this tip section 70 has a tapered cylinder shape where the thickness decreases gradually toward the tip. On the other hand, as shown in FIG. 7 the remaining base section, excluding this tip section, is entirely constituted by a multi-layer structure in which an inner resin layer 72 and outer resin layer 74 are integrally laminated on top of each other. In this embodiment, the inner resin layer 72 is formed, for example, by polyimide resin offering relatively high rigidity. The outer resin layer 74 is formed, for example, by the same flexible polyamide resin used in the tip section.

This way, the support tube 62 exhibits appropriate rigidity in the base section where the inner resin layer 72 and outer resin layer 74 are integrally laminated on top of each other, while ensuring sufficiently high flexibility or elasticity in the tip section 70 comprising only the flexible resin layer. As a result, damage to the interior surface of blood vessels can be prevented when the main tube 2 is inserted into the blood vessels, which may otherwise occur due to contact between the interior surface and the tip of the support tube 62 branching from the distal section 4 of the main tube 2. Also, as explained later the structure is designed so that the supporting force of the second guide wire 34 inserted into the continuous lumen 64 is ensured in a stable manner. Furthermore, the pushability of the support tube 62 into a branching blood vessel also improve. To be specific, when the support tube 62 is inserted into a branching blood vessel, the pushing force acting in the insertion direction and transmitted via the main tube 2 is efficiently transmitted to the support tube 62, thereby allowing the support tube 62 to be inserted smoothly into the branching blood vessel.

The structure of this support tube 62 is not at all limited to the one described above, and the entire part may have a single-layer structure comprising one type of resin layer, or the entire part may have a multi-layer structure comprising multiple types of resin layers laminated on top of each other. The support tube 62 can also be constituted by a flexible metal or composite tube formed by Ni—Ti alloy or any other superelastic alloy material, or stainless or any other metal material, used individually or in combination of any resin material, etc.

Also, as shown in FIGS. 2 and 3 a marker tube 76 is affixed at the tip of the support tube 62. This marker tube 76 is formed, for example, by a radio opaque material such as gold, platinum or platinum rhodium alloy, just like the marker tube 22 affixed in the distal section 4 of the main tube 2. This way, when the main tube 2 is inserted into blood vessels, the position of the marker tube 76 affixed at the tip of the support tube 62 can be identified by X-ray fluoroscopy. This permits easy identification of the position of the tip of the support tube 62 in the blood vessels.

Here, the support tube 62 having this structure is integrated with the distal end of the second guide wire insertion section 35 in a condition where the continuous lumen 64 is positioned so as to connect to the second guide wire lumen 52, with the opening on base side 68 in the continuous lumen 64 corresponding to the position of the opening on distal side 58 in the second guide wire lumen 52. Because of this, the support tube 62 is extended forward to the position where the opening on tip side 66 aligns side by side with the projection hole 14 in a condition where the support tube 62 branches from the distal section 4 of the main tube 2 with the tip of the support tube 62 providing a free end. And, the extension section of the second guide wire 34 extending out of the opening on distal side 58 in the second guide wire lumen 52 is inserted into this support tube 62 and supported.

Next, a method of injecting specified reagent into a necrotic lesion or the like in the cardiac muscle using a reagent injection catheter conforming to this embodiment is explained below.

As a specific example of implementing a reagent injection therapy using such reagent injection catheter, first the first guide wire 32 and second guide wire 34 are inserted into a main blood vessel 80 at the surface of a cardiac muscle 78, and into a branching blood vessel 82 that branches from this main blood vessel 80, respectively. At this time, the entire operation of inserting the first guide wire 32 and second guide wire 34 into the respective blood vessels 80, 82 is performed manually.

Next, the rear end of the first guide wire 32 to be projected out of the patient's body is inserted into the first guide wire lumen 38 through the opening on distal side 47, while at the same time this rear end is extended out of the opening on proximal side 48. On the other hand, the rear end of the second guide wire 34 to be projected out of the patient's body is inserted into the continuous lumen 64 through the opening on tip side 66 in the support tube 62, while at the same time this rear end is extended out of the opening on proximal side 60 in the second guide wire lumen 52. This way, the first guide wire 32 is inserted into the first guide wire lumen 38 by means of the monorail method in a condition movable in the axial direction, or specifically in a condition permitting advancing and retracting. Also, the second guide wire 34 is also inserted into the continuous lumen 64 and second guide wire lumen 52 by means of the monorail method in a condition permitting advancing and retracting.

Thereafter, the main tube 2 is inserted into the main blood vessel 80 along the first and second guide wires 32, 34. At this time, the orientation of the main tube 2 must be adjusted in advance so that the projection hole 14 will open toward the surface of the cardiac muscle 78. Also, the tip section of the needlelike tubular body 3 is inserted into the needlelike tubular body lumen 10 over a certain length.

Figure 15:
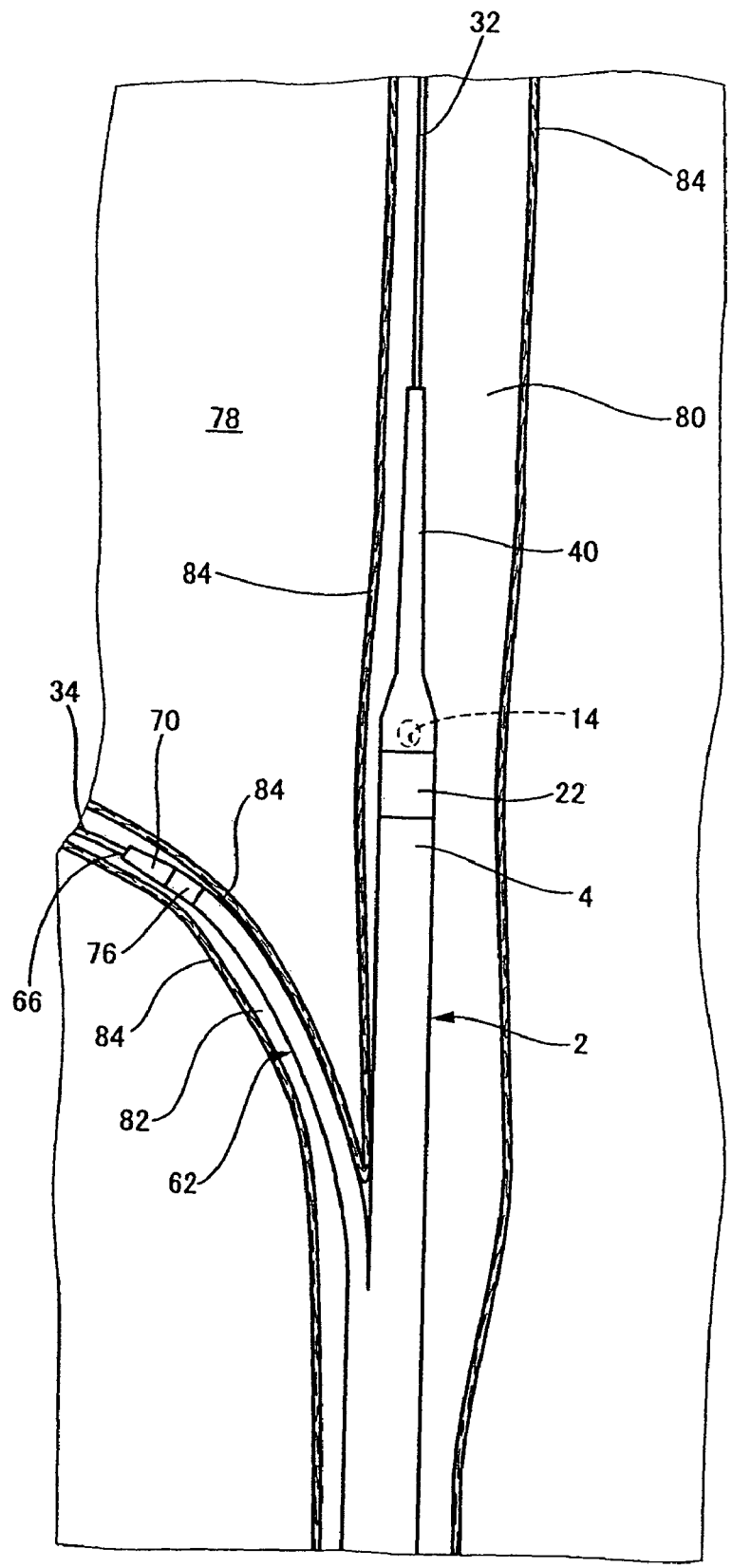
FIG. 15 is an explanatory drawing illustrating another example of operation of injecting specified reagent into a lesion in the cardiac muscle using the reagent injection apparatus shown in FIG. 1.

Then, as shown in FIG. 15, the main tube 2 is advanced through the main blood vessel 80 until the support tube 62 is guided by the second guide wire 34 and inserted and positioned in the branching blood vessel 82. At this time, while the main tube 2 is advanced through the main blood vessel 80, even when the circumferential position of the main tube 2 changes from the position adjusted at the start of operation, such displacement of the main tube 2 in the circumferential direction is corrected and the normal position adjusted at the start of operation is restored once the support tube 62 is inserted and positioned in the branching blood vessel 82. This way, the projection hole 14 provided in the main tube 2 is automatically positioned in such a way that it opens toward the surface of the cardiac muscle 78.

Also, this operation is performed while checking on a monitor or by other means under X-ray fluoroscopy the positions of the marker tubes 22, 76 affixed in the immediate vicinity of the projection hole 14 in the main tube 2, and at the tip of the support tube 62, respectively. This operation is deemed complete when the support tube 62 has been inserted and positioned in the branching blood vessel 82 and when it is confirmed that the projection hole 14 in the main tube 2 has reached the specified location in the main blood vessel 80.

By the way, in this embodiment the flexibility of the main tube 2 increases gradually toward the distal end, and the tip projection section 40 provided at this distal end and the tip section of the support tube 62 both have flexibility higher than other section. Also, the reinforcement layer 20 comprising braided thin stainless wires is provided inside the main tube 2. Furthermore, a greater part of the main tube, including the proximal section 6 and intermediate section 8, has a small diameter and contains only a needlelike tubular body lumen 10, and moreover the positions of the needlelike tubular body lumen 10 and second guide wire lumen 52 in the distal section 4 are arranged strategically so that the cross-section of the distal section 4 can be minimized.

Therefore, this operation allows the main tube 2 and support tube 62 to be inserted smoothly and safely into the main blood vessel 80 and branching blood vessel 82, without damaging the interior surface of the main blood vessel 80 and branching blood vessel 82, or without disrupting the blood flows in these blood vessels. In addition, this operation achieves favorable pushability, torquability of rotational torque, kink resistance and other properties in an advantageous manner.

Also in this embodiment, the length of the second guide wire lumen 52 and that of the continuous lumen 64 are set to approx. 180 mm and 20 mm, respectively, and the total length of the two, or specifically the total length of the second guide wire insertion section 35 and support tube 62, is roughly the same as or shorter than the length from the heart to the aortic arch in an average adult. For this reason, when the main tube 2 is inserted through to a specified location in the main blood vessel 80 in this operation, flexing of the second guide wire 34's insertion section along the aortic arch can be prevented. As a result, the sliding resistance during advancing or retracting of the second guide wire 34 in the second guide wire lumen 52 can be reduced in an advantageous manner, and thus the second guide wire 34 can be advanced or retracted more smoothly in this operation. Incidentally, the total length of the second guide wire lumen 52 and continuous lumen 64 should desirably be set to 200 mm or less, in order to ensure smooth advancing and retracting of the second guide wire 34 inside the second guide wire lumen 52 and continuous lumen 64.

Also under this operation, the operator, while performing the actual technique, selects a branching blood vessel 82 providing more favorable conditions than the rest of the many branching blood vessels 82 connecting from the main blood vessel 80, and inserts the second guide wire 34 into the selected branching blood vessel 82 by advancing and retracting it inside the second guide wire lumen 52 and continuous lumen 64. At this time, because the total length of the second guide wire lumen 52 and continuous lumen 64 through which the second guide wire 34 is inserted is sufficiently long, falling-off of the second guide wire 34 from these lumens 52, 64 can be effectively prevented during advancing or retracting movement under this operation.

Furthermore in this operation, the length of the support tube 62 is adjusted to 20 mm, and this facilitates easier insertion of the support tube 62 into the branching blood vessel 82. Also, the second guide wire 34 inserted into the branching blood vessel 82 is stably supported by the support tube 62 with greater supporting force. Here, the length of the support tube 62 should desirably be set to 40 mm or less in order to ensure easy insertion of the support tube 62 into the branching blood vessel 82. Also to ensure sufficient supporting force by the support tube 62 that has been inserted into the branching blood vessel 82, the length of the support tube 62 should desirably be set to 10 mm or more.

Moreover when the second guide wire 34 is advanced or retracted with respect to the support tube 62 in this operation, the second guide wire 34 moves sideway into the branching blood vessel 82 along the support tube 62. Therefore, the second guide wire 34 curves or flexes near the connection location with the continuous lumen 64 in the second guide wire lumen 52, or specifically in the distal end section of the second guide wire insertion section 35. As a result, the internal surface of the second guide wire lumen 52 is pressured by the curved or flexed section of the second guide wire 34. However, partly because the total length of the second guide wire lumen 52 is sufficiently long, and partly because the distal end section of the second guide wire insertion section 35 has an inner resin layer 54 made of polyimide resin offering relatively high rigidity, the distal end section of the second guide wire insertion section 35, or main tube 2 with which the distal end section is integrally formed, will not undergo curving or flexing deformation due to the pressure from the second guide wire 34. As a result, this operation can be performed more smoothly. For reference, the total length of the second guide wire lumen 52 should preferably be set to 20 mm or more in order to prevent, in a more reliable manner, any curving or flexing deformation of the main tube 2 due to the pressure from the second guide wire 34.

As explained above, this operation causes the first guide wire 32 and second guide wire 34 to be inserted and positioned in the main blood vessel 80 and branching blood vessel 82, respectively, in a condition where the guide wires are inserted through both the first guide wire lumen 38 and second guide wire lumen 52 in the main tube 2, as well as through the continuous lumen 52 in the support tube 62, respectively, and as a result the plane S is formed by these first guide wire 32 and second guide wire 34, as shown in FIG. 10. Also, the needle 24 of the needlelike tubular body 3 is virtually positioned inside this plane S.

As described above, the section where the first guide wire 32 and second guide wire 34 extend side by side in parallel, on the proximal side of the projection hole 14 in the distal section 4 of the main tube 2, has a length of approx. 30 mm. Therefore, the plane S is formed by these first guide wire 32 and second guide wire 34 in a more reliable manner. To reliably form this plane S in this way, the section where the first guide wire 32 and second guide wire 34 extend side by side in parallel, or in other words the section where the first guide wire lumen 38 and second guide wire lumen 52 extend in parallel within the distal section 4 of the main tube 2, should preferably be set to 10 mm or more. Also in this embodiment, the length of this section is set to 30 mm so as to prevent the first guide wire lumen 38 from becoming excessively long.

Figure 16:
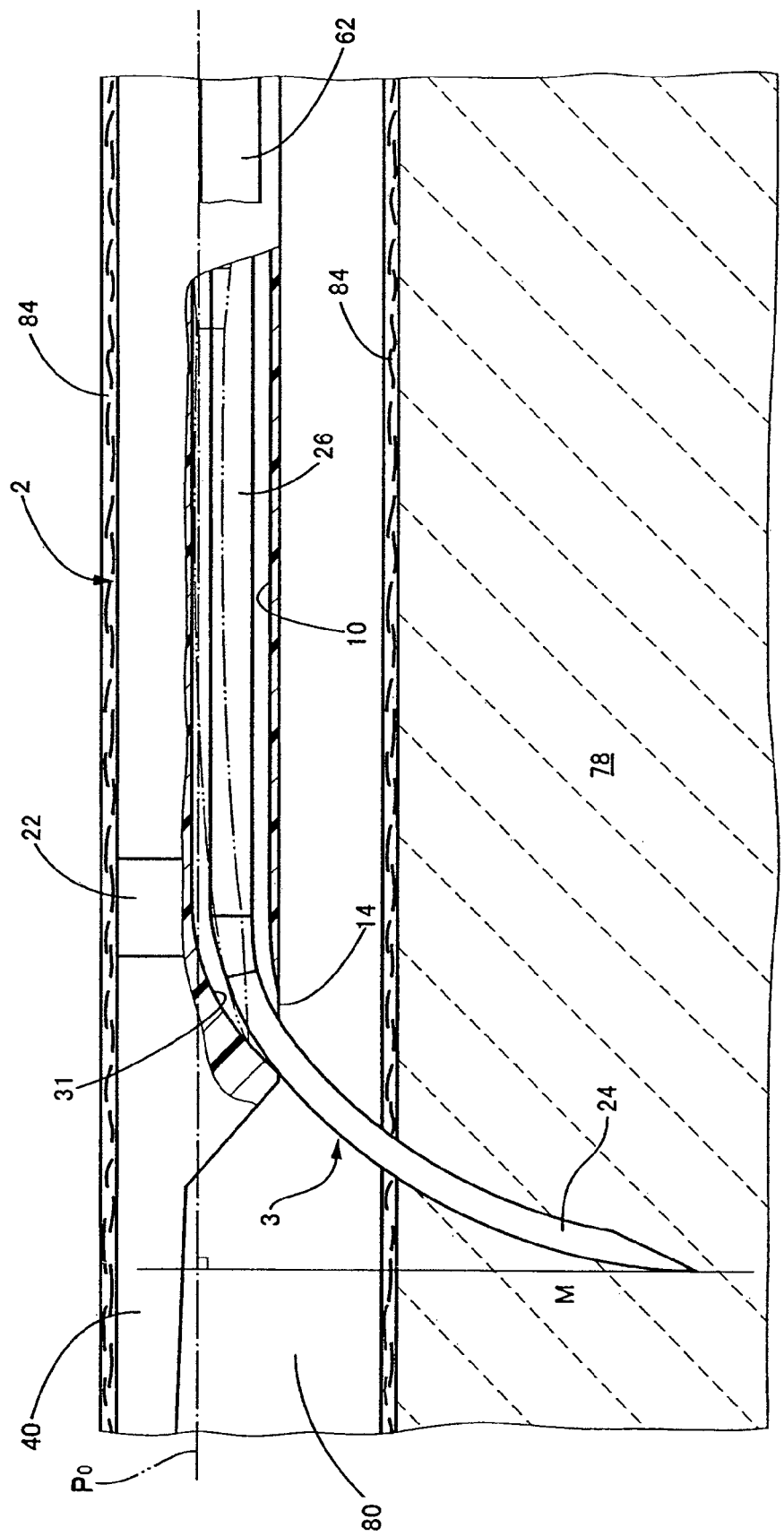
FIG. 16 is an explanatory drawing illustrating a yet another example of operation of injecting specified reagent into a lesion in the cardiac muscle using the reagent injection apparatus shown in FIG. 1.

Next, the needlelike tubular body 3 is advanced through the needlelike tubular body lumen 10 in the main tube 2. Thereafter when the needle 24 of the needlelike tubular body 3 reaches the distal end of the needlelike tubular body lumen 10, the needle 24 slides along the guide surface 31 provided in the distal end and projects outward from the projection hole 14, as indicated by the two-dot chain line and solid line in FIG. 16.

Also through this operation, the needle 24 of the needlelike tubular body 3 that has been projected from the projection hole 14 in the main tube 2 is operated to pierce through a blood vessel wall 84 of the main blood vessel 80 and ultimately puncture a specified location of lesion in the cardiac muscle 78. For your reference, the aforementioned operation to project the needle 24 by means of advancing movement through the needlelike tubular body 3, and to consequently puncture the cardiac muscle, is performed manually or by using a known screw mechanism or other appropriate means.

As an added note, as described above this embodiment causes the needle 24 of the needlelike tubular body 3 to be projected from the projection hole 14 in a direction virtually perpendicular to the extension directions of the first guide wire 32 and second guide wire 34 in a condition where the first guide wire 32 and second guide wire 34 are respectively inserted into the main blood vessel 80 and branching blood vessel 82 running at the surface of the cardiac muscle 78. In this way, the projected needle 24 punctures the cardiac muscle 78.

Because of this, the plane S formed by the first guide wire 32 and second guide wire 34 virtually represents the surface of the cardiac muscle 78, as shown in FIG. 10. Also, the vector V extending in the insertion direction of the needle 24 of the needlelike tubular body 3 into the cardiac muscle 78 forms, with the center axis $P_0$ of the main tube 2, a different plane U that crosses with the plane S at right angles. Furthermore, this vector V is divided into two vectors: the vector Vv extending perpendicularly to the plane S, and the vector Vh extending forward along the center axis $P_0$ of the main tube 2. In reality, the human heart has a complex curved surface and thus S actually becomes a curved surface. Here, however, it should be understood that S approximates a plane for the purpose of simplifying the explanation.

On the other hand, the reactive force (reactive force of puncturing) N, which is exerted upon the main tube 2 through the needle 24 in the direction opposite to the insertion direction of the needle 24 when the needle 24 enters the cardiac muscle 78, has roughly the same magnitude as the vector Vv extending perpendicularly to the plane S, and acts in the opposite direction to the direction of the vector Vv.

Consequently, here the reactive force of puncturing N that generates when the needle 24 enters the cardiac muscle 78 is divided into two components and received by the first guide wire 32 and second guide wire 34, respectively, within the plane S formed by the first guide wire 32 and second guide wire 34.

Also, these first guide wire 32 and second guide wire 34 are positioned in such a way that they extend side by side in parallel in the distal section 4 of the main tube 2 before the point where the second guide wire 34 is inserted into the continuous lumen 64 in the support tube 62. For this reason, the reactive force of puncturing N can be received in a more stable manner virtually within the plane S formed by first guide wire 32 and second guide wire 34.

In addition, in this operation the support tube 62, which supports the extension section of the second guide wire 34 from the main tube 2 (second guide wire insertion section 35), is also inserted and positioned in the branching blood vessel 82, in addition to the first guide wire 32 inserted into the main blood vessel 80 and the second guide wire 34 inserted into the branching blood vessel 82. This way, the reactive force of puncturing N that generates when the needle 24 enters the cardiac muscle 78 is also received reliably not only by the first guide wire 32 and second guide wire 34, but also by the support tube 62.

This further prevents, in a more advantageous manner, rotation of the main tube 2 around the axis inside the main blood vessel 80 due to the aforementioned reactive force of puncturing, compared to when only the first guide wire 32 and second guide wire 34 are inserted into the main blood vessel 80 and branching blood vessel 82, respectively.

Then, once the needle 24 that thus puncturing the lesion in the cardiac muscle 78 has reached a specified position in the lesion, the movement of the needlelike tubular body 3 ends. Thereafter, a reagent containing cells or growth factor or any other substance to regenerate the cardiac muscle 78 is introduced into the interior hole of the needlelike tubular body 3 through the syringe 30 connected to the connector 28 provided in the base section of the needlelike tubular body 3. Then, the reagent is discharged from the opening at the tip of the needle 24 and injected into the lesion in the cardiac muscle 78.

In the next step, the needlelike tubular body 3 is pulled backward once reagent has been injected in one location of lesion in the cardiac muscle 78, and the needle 24 is retracted into the main tube 2. Thereafter, this reagent injection operation is repeated several times in different locations of lesion in the cardiac muscle 78. This way, reagent is injected into multiple locations of lesion in the cardiac muscle 78.

Here, the length of the second guide wire lumen 52 from the opening on distal side 58 to the projection hole 14, or specifically the length from the branching point of the support tube 62 from the main tube 2 (second guide wire insertion section 35) to the projection hole 14, is identical to the length of the support tube 62. Because of this, the distance (dimension) to the puncturing position from the branching point of the branching blood vessel 82 from the main blood vessel 80 remains always the same as the insertion length of the support tube 62 into the branching blood vessel 82, even when the puncturing location of the needle 24 in the cardiac muscle 78 is changed by moving the main tube 2 in the extending direction of the main blood vessel 80. As a result, stable supporting force of the second guide wire 34 by the support tube 62 can be ensured even when the puncturing location of the needle 24 in the cardiac muscle 78 is changed.

As explained above, the reagent injection catheter provided by this embodiment allows for stable puncturing of the cardiac muscle 78 using the needle 24 in a condition where the main tube 2 is placed in a specified position in the main blood vessel 80 and thus rotation of the main tube 2 due to the reactive force of puncturing is prevented, even when the apparatus is not equipped with a balloon or any other means attached to conventional catheters.

Accordingly, the embodiment described above permits puncturing of a specified location of lesion in the cardiac muscle 78 using the needle 24 in a smoother and more reliable manner, by eliminating the need for a balloon and also achieving, in an advantageous manner, diameter or size reduction of the reagent injection catheter having the first and second guide wires 32, 34 through the use of the monorail method. As a result, reagent can be injected into a specified location in the cardiac muscle 78 in an easier, safer and more accurate manner.

Here, the reagent injection catheter provided by this embodiment can be produced, for example, in the manner described below.

Figure 17:
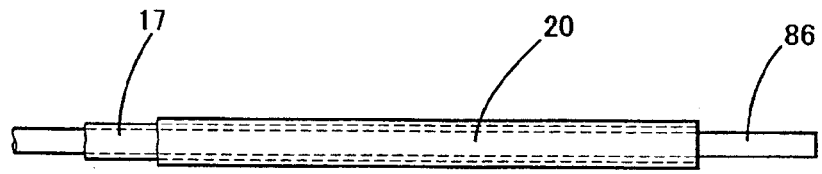
FIG. 17 is a drawing for explaining an example of a step of producing a reagent injection apparatus in accordance with the present invention.

To be specific, first a reinforcement layer 20 comprising thin stainless braided wires is attached onto the exterior side of an inner resin layer 17 made of a resin tube extrusion-molded using PTFE resin material, as shown in FIG. 17. A core metal 86 is inserted into an interior hole in the inner resin layer 17 to which the reinforcement layer 20 has been attached.

Figure 18:
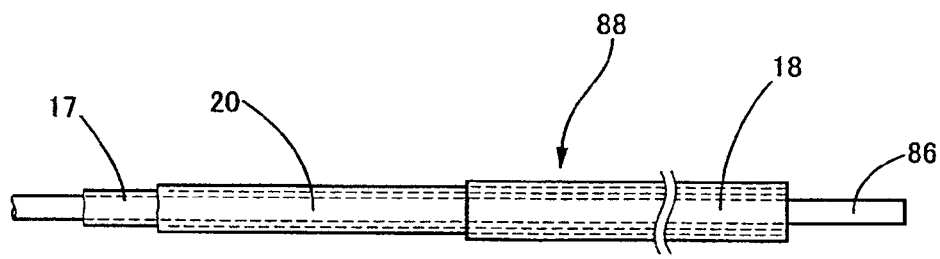
FIG. 18 is a drawing for explaining an example of a step performed after the one shown in FIG. 17.

Thereafter, as shown in FIG. 18 an outer resin layer 18 made of a resin tube extrusion-molded using polyamide resin material is attached onto the exterior side of the reinforcement layer 20 to produce a base tube 88. At this time, the outer resin layer 18 is not attached at one end of the base tube 88, and thus this end only comprises the inner resin layer 17 and reinforcement layer 20. Next, a known heat-shrinkable tube (not illustrated) is covered onto the base tube 88, after which the heat-shrinkable tube and base tube 88 are shrunk under heat using a known method. Thereafter, the heat-shrinkable tube is removed to produce a long main tube 2 having a multi-layer structure comprising the inner resin layer 17, reinforcement layer 20 and outer resin layer 18 laminated integrally on top of each other. In this process, a needlelike tubular body lumen 10 is also formed inside the main tube 2 from the interior hole in the inner resin layer 17.

Figure 19:
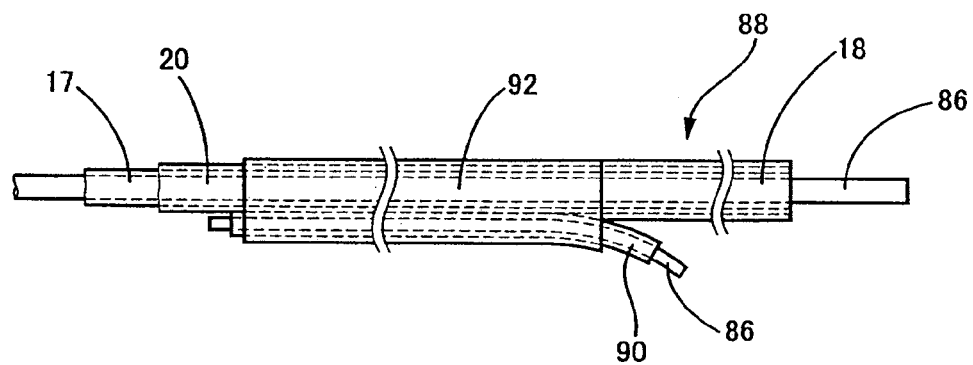
FIG. 19 is a drawing for explaining an example of a step performed after the one shown in FIG. 18.

On the other hand, as shown in FIG. 19 another process involving extrusion molding using polyethylene resin material is performed separately from the above production process of the main tube 2 to produce an inner tube 90 that comprises an inner resin layer 54 in the proximal section of a second guide wire insertion tube 50. At the same time, extrusion molding is performed using polyamide resin material to produce an outer tube 92 that comprises an outer resin layer 56 in the proximal section of the second guide wire insertion tube 50. Thereafter, the inner tube 90 is positioned in such a way that it extends side by side in parallel with the end of the main tube 2 where the external resin layer 18 has not been laminated. In this condition, the outer tube 92 is set to cover over the inner tube 90 and the end of the main tube 2, after which the outer tube 92 and inner tube 90 are shrunk under heat using a known method and welded together. Upon completion of this heat shrinking operation, the section of the inner tube 90 protruding from the outer tube 92 is cut off.

Figure 20:
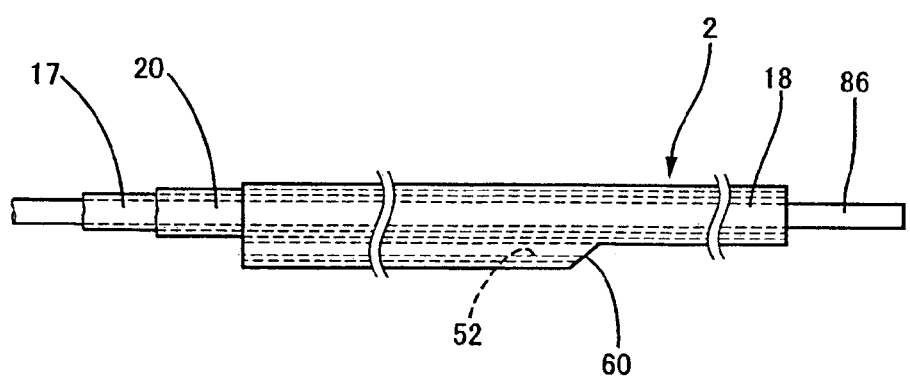
FIG. 20 is a drawing for explaining an example of a step performed after the one shown in FIG. 19.

This way, as shown in FIG. 20 the proximal section of the second guide wire insertion tube 50, having a multi-layer structure where the inner resin layer 54 made of polyethylene resin and outer resin layer 56 made of polyamide resin are laminated on top of each other, is integrated with the end portion, or specifically the distal section 4, of the main tube 2. Inside this second guide wire insertion tube 50, or specifically inside the interior hole in the inner tube 90, the proximal section of a second guide wire lumen 52 is formed. Furthermore, an opening on proximal side 60 in the second guide wire lumen 52 is formed, by means of cutting out the inner tube 90, at the proximal end of the second guide wire insertion tube 50.

Figure 21:
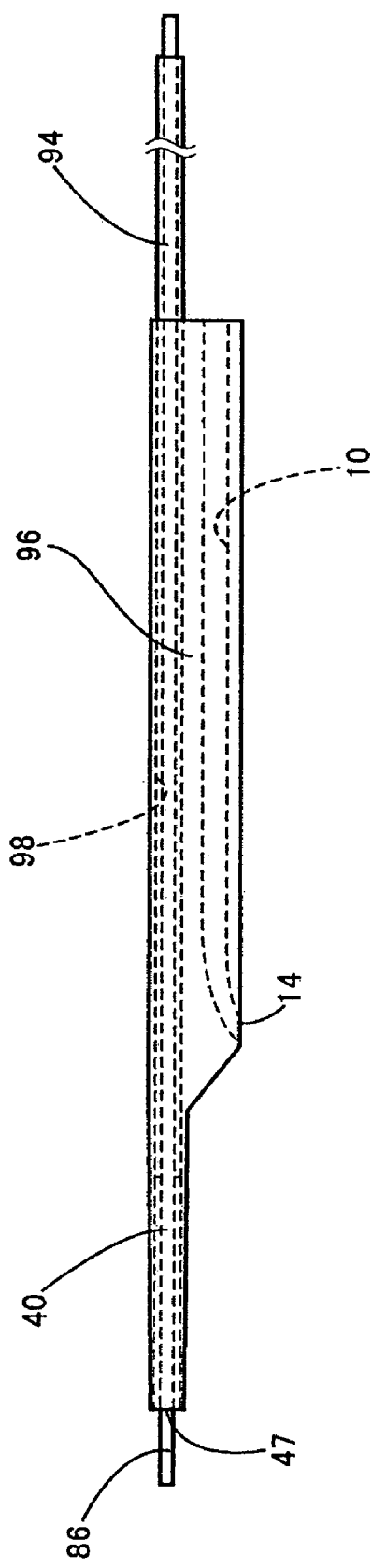
FIG. 21 is a drawing for explaining another example of a step of producing a reagent injection apparatus in accordance with the present invention.

Separately from the above operations, extrusion molding is performed using polyethylene resin material to produce an inner tube 94 that comprises an inner resin layer 44 of a first guide wire insertion tube 36, as shown in FIG. 21. At the same time, extrusion molding is performed using polyamide resin material to produce an outer tube 96 that comprises an outer resin layer 46 of the first guide wire insertion tube 36.

In this outer tube 96, an insertion hole 98 through which to insert the inner tube 94 is formed over the entire length. The distal end of the outer tube 96 is integrated with a tip projection section 40 having a tapered cylinder shape that becomes gradually thinner toward the tip, in a manner allowing the insertion hole 98 to run through its interior. This section except for the distal end is formed to have an outer diameter that is greater than that of the main tube 2 by a specified dimension. Also in this large-diameter section, a distal end section of a needlelike tubular body lumen 10 is formed in a manner extending side by side in parallel with the insertion hole 98. A projection hole 14 is also formed in this large-diameter distal end section.

Then, the inner tube 94 is inserted and positioned into the insertion hole 98 in the outer tube 96 thus formed, thereby forming a distal section of the first guide wire insertion tube 36. Also in this distal section of the first guide wire insertion tube 36, the distal section of the inner tube 94 is inserted into the insertion hole 98, while the proximal section of the inner tube 94 is positioned in such a way that it extends out of the opening on proximal side of the insertion hole 98.

Figure 22:
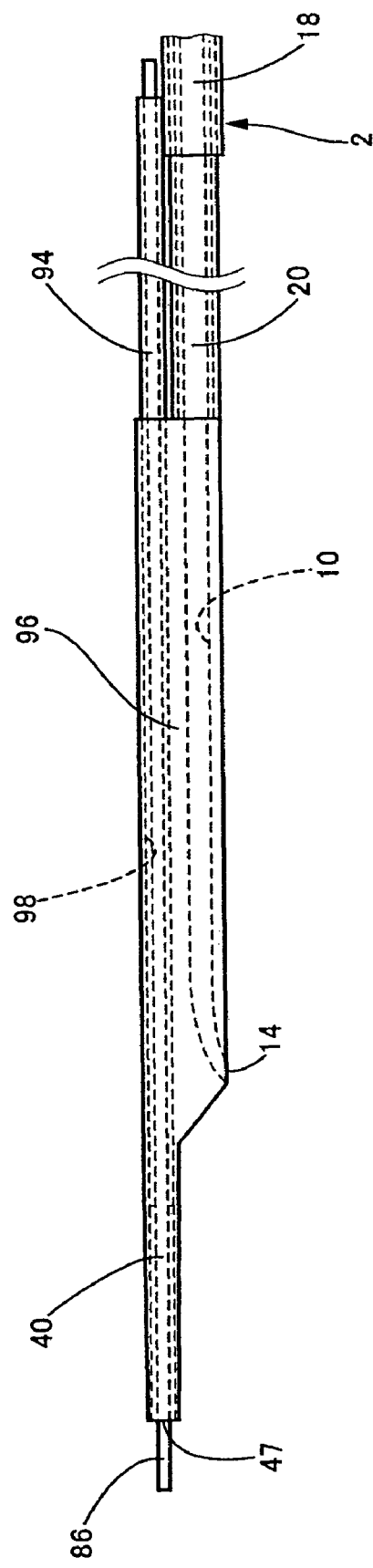
FIG. 22 is a drawing for explaining an example of a step performed after the one shown in FIG. 21.

Thereafter, the distal section of this first guide wire insertion tube 36 is integrated with the main tube 2 by means of welding, etc., so that the needlelike tubular body lumens 10 formed inside the respective tubes are butt-connected with each other, as shown in FIG. 22. At this time, the inner tube 94 extending out of the insertion hole 98 in the outer tube 96 for the first guide wire insertion tube 36 is positioned in such a way that it extends in the axial direction on the top face of the distal section 4 of the main tube 2.

Figure 23:
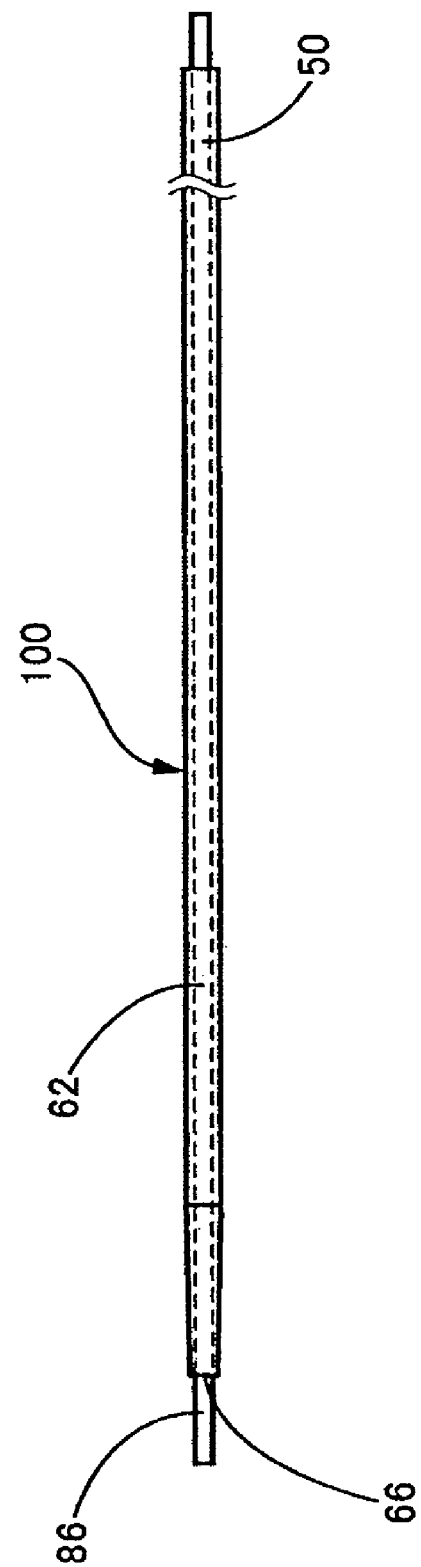
FIG. 23 is a drawing for explaining a yet another example of a step of producing a reagent injection apparatus in accordance with the present invention.

On the other hand, a resin tube 100 that integrally provides the distal section of the second guide wire insertion tube 50 and the support tube 62 is formed, through an operation separate from the production of the distal section of the first guide wire insertion tube 36, as shown in FIG. 23. As for this resin tube 100, its distal end section has a single-layer structure comprising only a flexible resin layer 70 made of polyamide resin material, as well as a tapered cylinder shape that gradually becomes thinner toward the tip. All other sections have a multi-layer structure where inner resin layers 54, 72 made of polyimide resin material and outer resin layers 56, 74 made of polyamide resin materials are laminated on top of each other.

Figure 24:
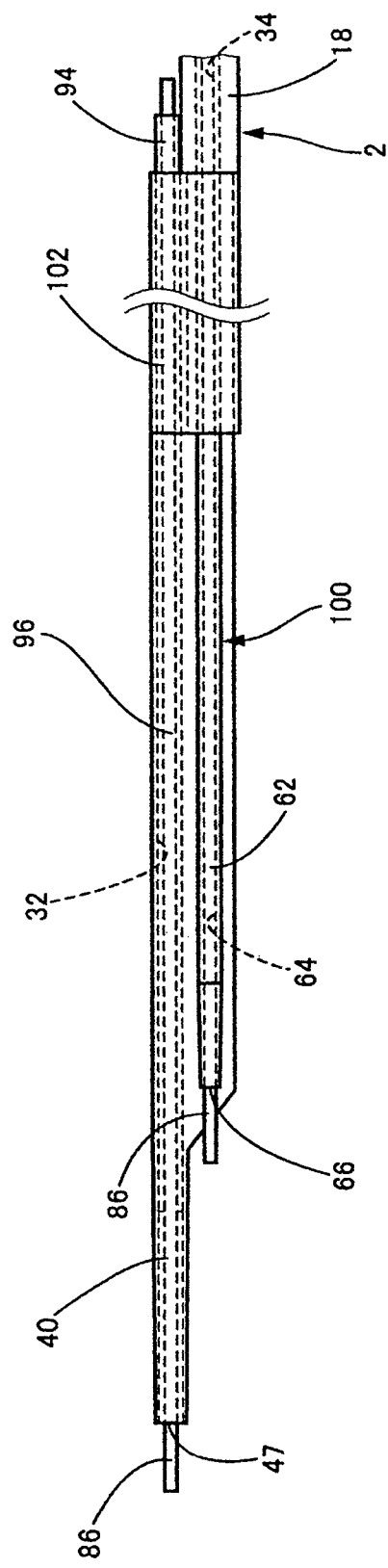
FIG. 24 is a drawing for explaining an example of a step performed after the one shown in FIG. 22.

Next, as shown in FIG. 24 the resin tube 100 thus produced is positioned in a manner extending in the axial direction, on side of the distal section 4 of the main tube 2 in the condition shown in FIG. 22. With the tubes placed in this condition, a separately formed cover tube 102 made of polyamide resin material is set to cover over the main tube 2 in such a way that the proximal section of the resin tube 100, except for the support tube 62, as well as the inner tube 94 extending out of the insertion hole 98 in the outer tube 96 for the first guide wire insertion tube 36, are both positioned inside the cover tube 102. Thereafter, the cover tube 102 is shrunk under heat and welded using a know method. As a result, the resin tube 100 and inner tube 94 are integrated with the main tube 2.

Thereafter, the proximal end of the inner tube 94 is cut off (not illustrated), and an opening on proximal side 48 in the first guide wire lumen is formed by utilizing this cutout section.

Through the aforementioned steps, the first guide wire insertion tube 36 and second guide wire insertion tube 50 are integrated on top and side of the distal section 4 of the main tube 2, while the support tube 62 is also integrated while maintaining its tip as a free end. Then, the needlelike tubular body lumen 10 is formed inside the main tube 2, and the first guide wire lumen 38 and second guide wire lumen 52 are formed in such a way that they are positioned on top and side of the needlelike tubular body lumen 10. Furthermore, the openings on distal side and proximal side 47, 58, 48, 60 are formed in the first and second guide wire lumens 38, 52 so that they open in the aforementioned positions, respectively.

Based on the embodiment method described above, a reagent injection catheter whose diameter or size can be reduced in an advantageous manner and which can be used to inject reagent safely and accurately into a specified location in the cardiac muscle 78 can be produced very easily.

The foregoing described specific structures conforming to the present invention. It should be noted, however, that these structures are presented as examples only and the present invention is not at all limited by any of the descriptions provide above.

For example, the outer periphery or exterior shape of the main tube 2 is not at all limited to the one illustrated above.

In addition, a reagent injection catheter conforming to the present invention can also be produced using a known method similar to any of the conventional methods.

Furthermore, the structures to partially differentiate the flexibility levels of the main tube 2 and support tube 62 are not specifically limited to those illustrated above.

As for the exterior of the main tube 2, it is certainly possible to attach an inflatable/deflatable balloon of a known structure. If such balloon is attached, the positional stability of the main tube 2 in the main blood vessel 80 can be enhanced in a more advantageous manner, and consequently puncturing operation using the needle, and ultimately reagent injection operation, can be implemented in a more stable and easier manner. If a balloon is attached on the exterior of the main tube 2, a passage (balloon lumen) must be provided in the main tube 2 for supplying saline solution or other liquid to inflate the balloon.

In the aforementioned embodiments, specific examples were given in which the present invention was applied to a reagent injection catheter used to inject reagent into lesions in the cardiac muscle. It should be noted, however, that it is clearly possible to also apply the present invention, in an advantageous manner, to reagent injection catheters used to inject reagent into the body tissues of various organs, including bone marrow, other than the cardiac muscle, or injection apparatuses not classified as catheters that are nonetheless used to inject reagent into lesions in the cardiac muscle as well as body tissues of various organs other than the cardiac muscle.

Although all possible variations are not listed herein, the present invention can be embodied in any modes incorporating various changes, modifications and improvements based on the knowledge of those skilled in the art. It goes without saying that these embodiments are also included in the scope of the present invention, as long as they do not deviate from the purpose of the present invention. Therefore, it should be clearly understood that the forms of the present invention are illustrative only and are not intended to limit the scope of the present invention.

In the present disclosure where conditions and/or structures are not specified, the skilled artisan in the art can readily provide such conditions and/or structures, in view of the present disclosure, as a matter of routine experimentation.

The present application claims priority to Japanese Patent Application No. JP2005-274423, filed Sep. 21, 2005, the disclosure of which is incorporated herein by reference in its entirety.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A reagent injection apparatus comprising:
   a main tube having flexibility, providing a needlelike tubular body lumen in an axial direction, and inserted into the patient's body;
   a needlelike tubular body made of a flexible thin tube through which specified reagent can flow, the needlelike tubular body inserted into the needlelike tubular body lumen of the main tube in a movable manner and its tip section projected outward from a projection hole provided in the main tube to puncture specified tissue in the patient's body, in order to inject the reagent into the body tissue;
   a first guide wire lumen extending in the axial direction in the main tube for receiving a first guide wire in a movable manner, and having a distal opening distal to the projection hole and a proximal opening proximal to the projection hole, at least the proximal opening being on a side of the main tube;
   a second guide wire lumen extending in the axial direction in the main tube for receiving a second guide wire in a movable manner, having proximal and distal openings, each of the proximal and distal openings of the second guide wire lumen being proximal to the projection hole, the proximal opening of the second guide wire lumen being opened in a side surface of the main tube, and the proximal opening of the first guide wire lumen being positioned between the proximal and distal openings of the second guide wire lumen;
   and
   a support tube having flexibility and having a tip section provided as a free end, the support tube provided in a manner branching from the main tube, and having a continuous lumen that continues to the second guide wire lumen through the distal opening of the second guide wire lumen, which is closer to the projection hole, wherein a part of the second guide wire extending from the distal opening of the second guide wire lumen, which is closer to the projection hole, is inserted into the continuous lumen in a movable manner.

2. The reagent injection apparatus according to claim 1, wherein a tip section of the support tube provided as a free end has higher flexibility than a base section of the support tube.

3. The reagent injection apparatus according to claim 2, wherein the tip section of the support tube has a single-layer structure comprising only a flexible resin layer, while the base section has a multi-layer structure in which the flexible resin layer is laminated on its interior or exterior side with a resin layer having rigidity higher than that of the flexible resin layer, so that the tip section has higher flexibility than the base section.

4. The reagent injection apparatus according to claim 1, wherein a section in which the needlelike tubular body lumen, first guide wire lumen and second guide wire lumen are placed in parallel with one another is at least 10 mm long.

5. The reagent injection apparatus according to claim 1, wherein the second guide wire lumen is at least 20 mm long.

6. The reagent injection apparatus according to claim 1, wherein the total length of the second guide wire lumen and continuous lumen is 200 mm or less.

7. The reagent injection apparatus according to claim 1, wherein the main tube comprises a multi-layer section in which an inner resin layer is laminated with an external resin layer having characteristics different from those of the inner resin layer.

8. The reagent injection apparatus according to claim 1, wherein the main tube has a multi-layer structure in which an inner resin layer is laminated on its exterior with a braided reinforcement layer made of resin or metal.

9. The reagent injection apparatus according to claim 1, wherein the main tube has a structure whereby the flexibility increases from the proximal of the main tube toward the distal of the main tube gradually or in steps.

10. The reagent injection apparatus according to claim 1, wherein the support tube has a length of 10 to 40 mm.

11. The reagent injection apparatus according to claim 1, wherein a marker made of a radio opaque material is provided in a distal section of the support tube.

12. The reagent injection apparatus according to claim 1, wherein the main tube has no balloon.

13. The reagent injection apparatus according to claim 1, wherein a center axis of the first guide wire lumen, a center axis of the needlelike tubular body lumen, a center axis of the main tube and a center of the projection hole are substantially aligned and laid on a same plane, and the second guide wire lumen is positioned out of said plane.

* * * * *